United States Patent
Hoshino et al.

(10) Patent No.: US 9,433,345 B2
(45) Date of Patent: Sep. 6, 2016

(54) CYCLODUCTION MEASUREMENT DEVICE, CYCLODUCTION MEASUREMENT METHOD, AND CYCLODUCTION MEASUREMENT PROGRAM

(71) Applicant: UNIVERSITY OF TSUKUBA, Tsukuba-shi, Ibaraki (JP)

(72) Inventors: Kiyoshi Hoshino, Tsukuba (JP); Hiroyuki Nakagomi, Tsukuba (JP)

(73) Assignee: UNIVERSITY OF TSUKUBA, Tsukuba (JP)

(*) Notice: Subject to any disclaimer, the term of this patent is extended or adjusted under 35 U.S.C. 154(b) by 0 days.

(21) Appl. No.: 14/380,912

(22) PCT Filed: Feb. 22, 2013

(86) PCT No.: PCT/JP2013/054609
§ 371 (c)(1),
(2) Date: Aug. 25, 2014

(87) PCT Pub. No.: WO2013/125707
PCT Pub. Date: Aug. 29, 2013

(65) Prior Publication Data
US 2015/0029461 A1 Jan. 29, 2015

(30) Foreign Application Priority Data
Feb. 24, 2012 (JP) .................. 2012-039403
Oct. 9, 2012 (JP) .................. 2012-224622

(51) Int. Cl.
A61B 3/14 (2006.01)
A61B 3/00 (2006.01)
A61B 3/113 (2006.01)
G06T 7/00 (2006.01)
G06K 9/00 (2006.01)

(52) U.S. Cl.
CPC ............. *A61B 3/0025* (2013.01); *A61B 3/113* (2013.01); *A61B 3/14* (2013.01); *G06K 9/00604* (2013.01); *G06T 7/0044* (2013.01); *G06T 2207/30041* (2013.01)

(58) Field of Classification Search
USPC .................................. 351/206, 246
See application file for complete search history.

(56) References Cited

U.S. PATENT DOCUMENTS
5,070,883 A 12/1991 Kasahara
2013/0162947 A1 6/2013 Spasovski FOREIGN PATENT DOCUMENTS
DE 102010032193 A1 1/2012
JP A-2-164335 6/1990
JP 2008-099716 A 5/2008

OTHER PUBLICATIONS

Hashimoto et al., "A Model of the Iris Pattern Stretches in Relation to Pupil Diameter and Its Application to Measurement of Roll Eye Movements," *Institute of Electronics, Information and Communication Engineers Transaction*, 2010, vol. J93-D, No. 1, pp. 39-46 (with translation).

International Search Report issued in International Patent Application No. PCT/JP2013/054609 mailed Mar. 19, 2013.

Oct. 6, 2015 Extended European Search Report issued in European Patent Application No. 13751309.9.

Sakashita et al. "Real-Time Measurement of Cycloduction Movement Based on Fast Ellipse Detection." Electronics and Communications in Japan. vol. 92, No. 11, pp. 9-18, 2009.

*Primary Examiner* — Jack Dinh
(74) *Attorney, Agent, or Firm* — Oliff PLC

(57) ABSTRACT

This cycloduction measurement device is provided with a blood vessel position recognition unit and a first angle calculation unit. The blood vessel position recognition unit recognizes the position of a blood vessel in a sclera region in an eye image, and acquires information pertaining to the position of the blood vessel. The first angle calculation unit calculates the angle of cycloduction on the basis of the first information pertaining to the position of a predetermined blood vessel acquired by the blood vessel position recognition unit during actual measurement of cycloduction, and a second information pertaining to the position of the predetermined blood vessel while in a reference state.

14 Claims, 15 Drawing Sheets

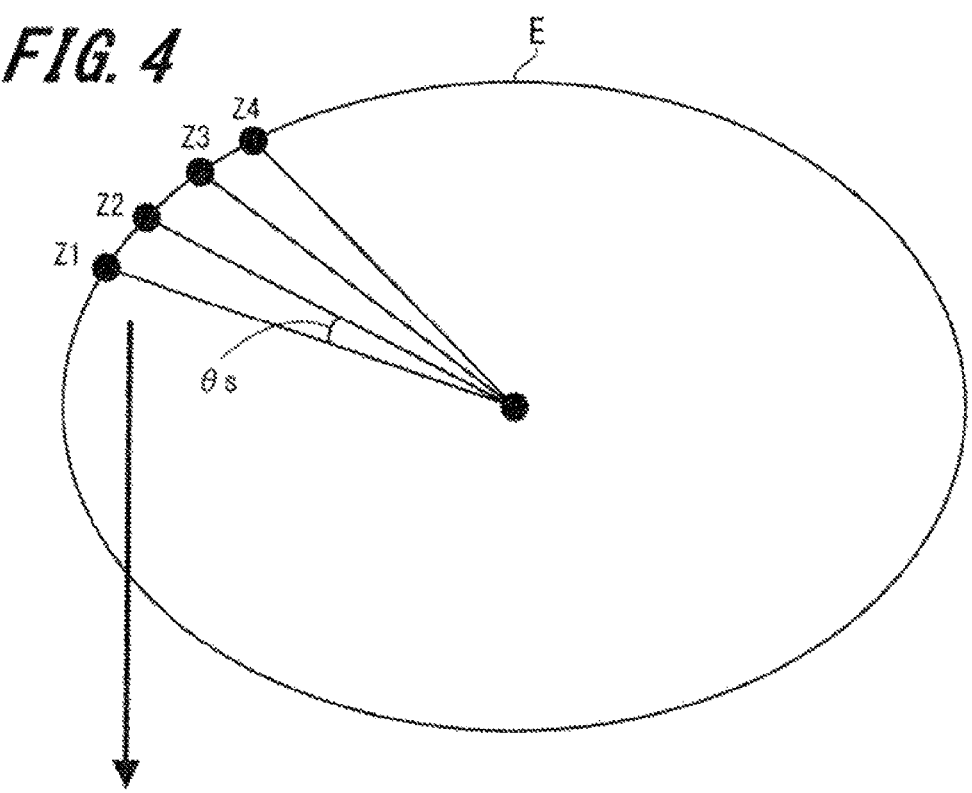

FIG. 14
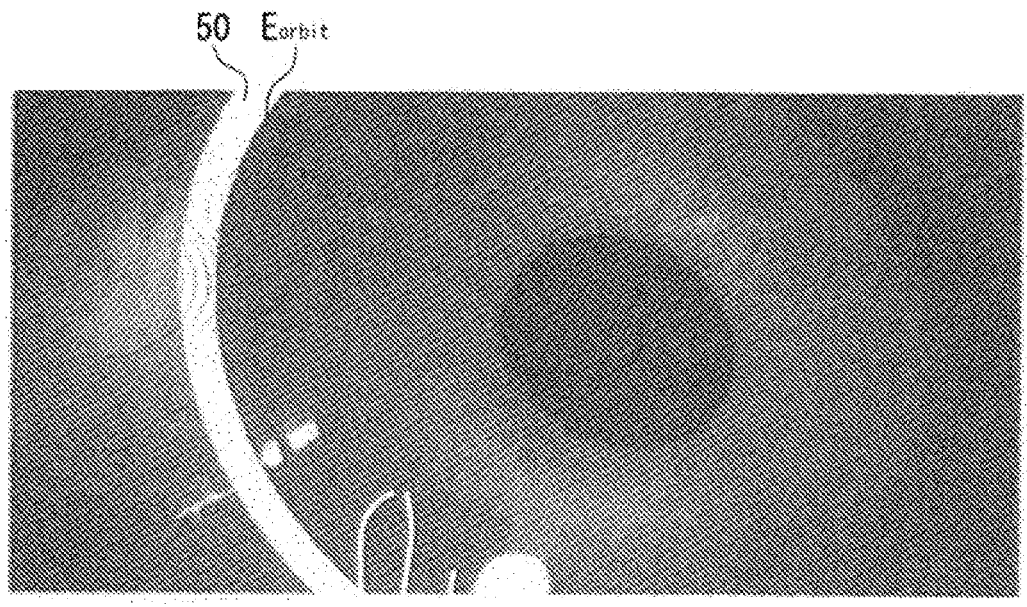
FIG. 15A  FIG. 15B  FIG. 15C
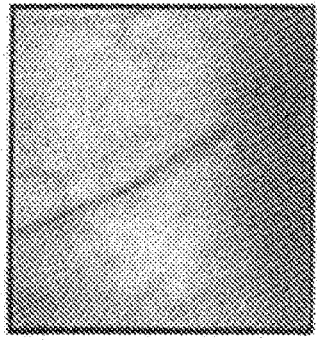 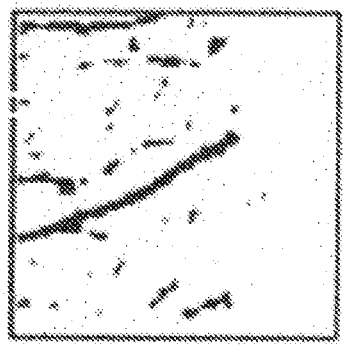 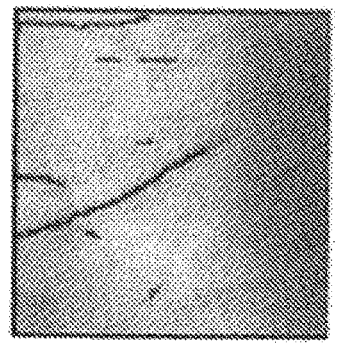

52 51 50

62
61

| PUPIL SIZE | ERROR OF CYCLODUCTION ANGLE (DEGREES) | STANDARD DEVIATION (DEGREES) |
|---|---|---|
| SMALL | 0.153 | 0.071 |
| MEDIUM | 0.192 | 0.192 |
| LARGE | 0.232 | 0.154 |

CYCLODUCTION MEASUREMENT DEVICE, CYCLODUCTION MEASUREMENT METHOD, AND CYCLODUCTION MEASUREMENT PROGRAM

TECHNICAL FIELD

The present invention relates to a cycloduction measurement device, a cycloduction measurement method, and a cycloduction measurement program.

BACKGROUND ART

An eyeball of an animal is not only rotatable vertically and horizontally, but also can rotate about the axis of the visual line direction. The rotation is referred to as "cycloduction". Cycloduction is generated by the action of trying to return to an original state when tilting the head. In addition, cycloduction is also generated when a person is feeling bad due to vehicle-induced or visually-induced motion sickness, for example, and thus the technique of measuring cycloduction can be useful at medical or nursing care fields.

As a cycloduction measurement method, there has been disclosed (see non-patent literature 1, for example) a method of recognizing a shading pattern of an iris image in an eye image (hereinafter, referred to iris shading pattern), and measuring cycloduction on the basis of the recognition result. In addition, the non-patent literature 1 also describes a technique of suppressing degradation of the measurement precision of cycloduction due to change of the pupil diameter by correcting the deformed iris shading pattern through the use of the fact that deformation of the iris shading pattern is proportional to the pupil diameter.

CITATION LIST

Non Patent Literature

NPL 1: Tsutomu Hashimoto, Yoshio Maki, Yusuke Sakashita, Junpei Nishiyama, Hironobu Fujiyoshi, Yutaka Hirata, "A Model of the Iris Pattern Stretches in Relation to Pupil Diameter and Its Application to Measurement of Roll Eye Movements", Institute of Electronics, Information and Communication Engineers Transaction, 2010, Vol. J93-D, No. 1, pp. 39-46

SUMMARY OF INVENTION

Technical Problem

However, in the aforementioned technical field, development of a technique that allows measurement of cycloduction with higher precision is desired. The present invention has been made in order to meet the request, and an object thereof is to provide a cycloduction measurement device, a cycloduction measurement method, and a cycloduction measurement program, which allow measurement of cycloduction with higher precision.

Solution to Problem

In order to solve the above problem, the cycloduction measurement device of the present invention has a blood vessel position recognition unit configured to recognize a position of a blood vessel in a sclera region in an eye image and acquire information pertaining to the position of the blood vessel; and a first angle calculation unit configured to calculate an angle of cycloduction, on the basis of a first information pertaining to a position of a predetermined blood vessel acquired by the blood vessel position recognition unit when actually measuring cycloduction and a second information pertaining to the position of the predetermined blood vessel in a reference state.

In the present specification, "sclera region" refers to a region including the sclera and the conjunctiva. In addition, "reference state" in the present specification refers to, for example, a state of the subject having no stress and being healthy, that is, a state in which the angle of cycloduction of the eyeball is considered to be zero degree.

In addition, the cycloduction measurement method of the present invention includes: recognizing a position of a predetermined blood vessel in a sclera region in an eye image acquired when actually measuring cycloduction, and acquiring a first information pertaining to the position of the predetermined blood vessel; and calculating an angle of cycloduction, on the basis of the first information and a second information pertaining to the position of the predetermined blood vessel in a reference state.

Furthermore, the cycloduction measurement program of the present invention is a cycloduction measurement program implemented in an information processing apparatus, for causing the information processing apparatus to perform the respective pieces of processing of the aforementioned cycloduction measurement method of the present invention.

Advantageous Effects of Invention

According to the above configuration of the present invention, cycloduction can be measured with higher precision.

BRIEF DESCRIPTION OF DRAWINGS

FIG. 4 is an explanatory diagram of a method of generating vector data in a virtual ellipse;

FIG. 14 illustrates a detection area when detecting end points of a plurality of conjunctival blood vessels in the second embodiment;

FIGS. 15A to 15C are explanatory diagrams of processing of extracting the end point of the conjunctival blood vessel in the second embodiment;

DESCRIPTION OF EMBODIMENTS

Hereinafter, various embodiments according to the present invention will be described, referring to the accompanying drawings. However, before that, there will be described a problem which may arise in the method of measuring cycloduction by recognizing, for example, the iris shading pattern, i.e., a radial pattern referred to as an iris pattern, which is proposed in the non-patent literature 1.

The iris shading pattern (iris pattern) has the following characteristic, for example. The contrast of the iris shading pattern is low. The position of the iris pattern moves along with constriction or dilation of the pupil. When the pupil dilates, the central part of the iris region, where the contrast is relatively high, disappears. Since the contrast is low at the periphery of the iris region which does not disappear along with pupil dilation, it often happens that sufficient resolution (precision) of the angle of cycloduction cannot be acquired.

Due to the aforementioned various characteristics, the cycloduction measurement method using the iris shading pattern may result in increased errors or disabled measurement when the pupil diameter of the eyeball significantly varies. Therefore, the present invention provides a cycloduction measurement technique which can measure cycloduction with high precision even when the pupil diameter of the eyeball significantly varies.

<1. First embodiment>

First, a cycloduction measurement device, a cycloduction measurement method, and a cycloduction measurement program according to a first embodiment of the present invention will be described.

[Hardware Configuration]

Figure 1:
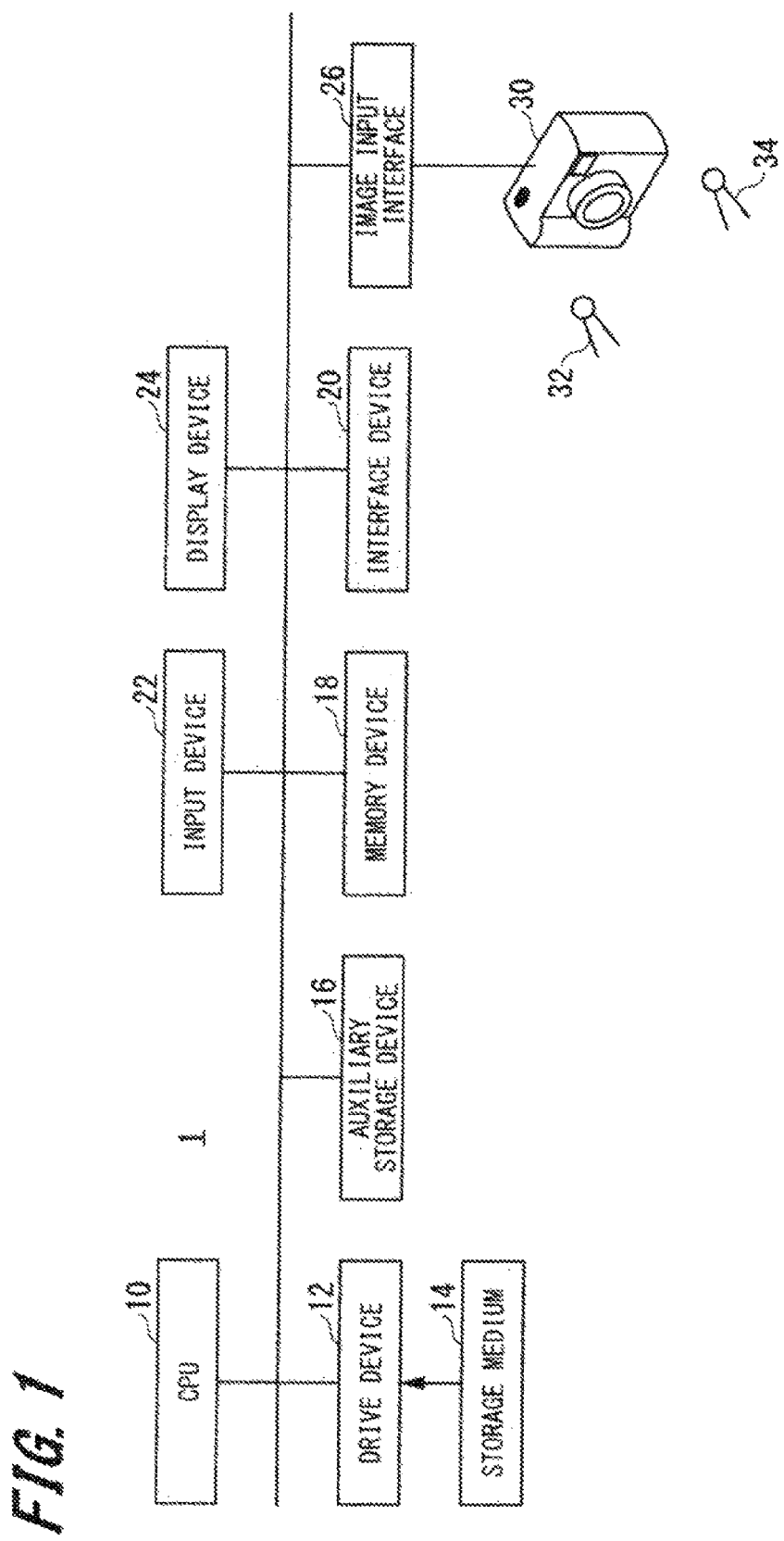
FIG. 1 is a hardware configuration diagram of a cycloduction measurement device 1 according to the first embodiment of the present invention.

FIG. 1 is a hardware configuration diagram of a cycloduction measurement device 1 according to the first embodiment. The cycloduction measurement device 1 includes, for example, a CPU (Central Processing Unit) 10, a drive device 12, an auxiliary storage device 16, a memory device 18, an interface device 20, an input device 22, a display device 24, and an image input interface 26. These components are connected to one another via a bus or a serial line.

The CPU 10 includes an arithmetic processing unit having, for example, a program counter, an instruction decoder, various operation devices, a LSU (Load Store Unit), general-purpose register, or the like.

The drive device 12 is a device configured to read programs or data from a storage medium 14 mounted therein. Meanwhile, in the present embodiment, the storage medium 14 is a portable storage medium such as a CD (Compact Disc), a DVD (Digital Versatile Disc), or a USB (Universal Serial Bus) memory. In addition, the auxiliary storage device 16 includes, for example, a HDD (Hard Disk Drive), a flash memory, or the like.

In the present embodiment, when the storage medium 14 having a program recorded thereon is mounted on the drive device 12, the program is installed from the storage medium 14 to the auxiliary storage device 16 via the drive device 12. Meanwhile, the installation method of programs is not limited to the example. For example, the interface device 20 may download a program from another computer via a network and install the downloaded program to the auxiliary storage device 16. Meanwhile, the network includes the Internet, a LAN (Local Area Network), a wireless network, or the like. In addition, programs may be preliminarily stored (implemented) in the auxiliary storage device 16, or a ROM (Read Only Memory) which is not illustrated, for example, when shipping the cycloduction measurement device 1.

The CPU 10 executes the various programs installed as described above or the preliminarily stored various programs to thereby realize various functions (various processing) described below in the cycloduction measurement device 1 of the present embodiment.

The memory device 18 includes a storage device such as, for example, a RAM (Random Access Memory), an EEPROM (Electrically Erasable and Programmable Read Only Memory), or the like. In addition, the interface device 20 is connected to the aforementioned various networks, and performs input/output operation of predetermined data, programs or the like from and to various external devices via the networks.

The input device 22 includes various input operation devices such as a keyboard, a mouse, a button, a touchpad, a touch panel, or a microphone. In addition, the display device 24 includes a presentation device such as a LCD (Liquid Crystal Display), or a CRT (Cathode Ray Tube). Meanwhile, the cycloduction measurement device 1 may have various output devices such as, for example, a printer, a loud speaker, or the like, besides the display device 24.

The image input interface 26 is connected to a camera 30. In addition, the image input interface 26 outputs image data input from the camera 30 to the memory device 18 or the auxiliary storage device 16.

The camera 30, which is an image capturing device such as a CCD (Charge Coupled Device) camera or a CMOS (Complementary Metal Oxide Semiconductor) camera, outputs data of the captured image to the image input interface 26. Meanwhile, the image may be a still image or a video image.

In the present embodiment, photographing of a subject's eyeball is conducted with the camera 30. At this time, the eyeball is irradiated with the light beams emitted from each of an infrared LED (Light Emitting Diode) 32 and a blue LED 34. The infrared LED 32 irradiates the eyeball with infrared rays in order to emphasize the pupil and photograph the iris shading pattern with high precision. In addition, the blue LED 34 irradiates the sclera region (area including the sclera and the conjunctiva) of the eyeball with blue light in order to raise the contrast of the conjunctival blood vessel in the eyeball (hereinafter, simply referred to as blood vessel). The burden imposed on the subject when photographing the eyeball can be reduced by narrowing down the irradiation range of the blue LED 34 to the sclera region of the eyeball.

[Functional Configuration]

Figure 2:
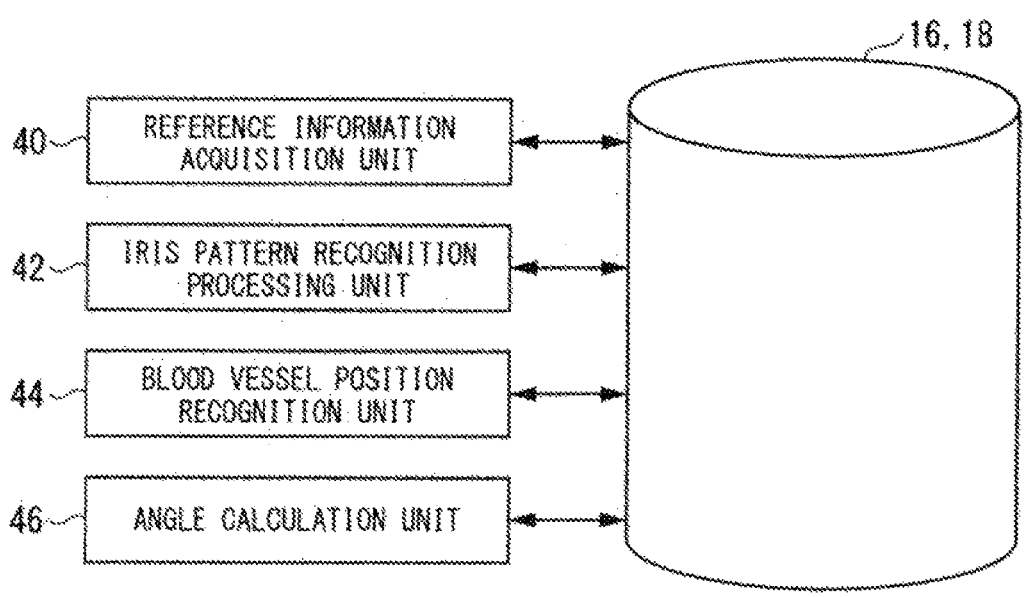
FIG. 2 is a functional configuration diagram of the cycloduction measurement device 1 according to the first embodiment of the present invention.

FIG. 2 is a functional configuration diagram of the cycloduction measurement device 1 of the present embodiment. The cycloduction measurement device 1 has a reference information acquisition unit 40, an iris pattern recognition processing unit 42 (second angle calculation unit), a blood vessel position recognition unit 44, and an angle calculation unit 46 (first angle calculation unit), as functional blocks that function by executing programs by the CPU 10. In addition, the functional blocks input and output various pieces of information (data) from and to, for example, the memory device 13 or the auxiliary storage device 16. The memory device 18 and the auxiliary storage device 16 then store various pieces of information output from each of the functional blocks.

The functional blocks can be configured by software. In such case, each of the functional blocks may be a block carried out by programs explicitly separated from one another, or may be a block carried out by programs called from other programs such as subroutines or functions. In addition, a part or all of the functional blocks may be configured by hardware such as a LSI (Large Scale Integrated circuit), an IC (Integrated Circuit) or a FPGA (Field Programmable Gate Array).

[Cycloduction Measurement Method]

(1) Outline of the Cycloduction Measurement Method

Next, the cycloduction measurement method according to the present embodiment will be specifically described, while explaining various processing performed in the respective functional blocks illustrated in FIG. 2. First, the cycloduction measurement method according to the present embodiment will be outlined.

The cycloduction measurement method according to the present embodiment first selects, in the reference state, a predetermined blood vessel (single blood vessel) located in the vicinity of the boundary between the iris region and the sclera region in an eye image in the reference state, and acquires position information of the end point at the pupil side of the selected blood vessel (target end point Otgt0 described below). Subsequently, in actual measurement of cycloduction, the angle of cycloduction (first angle of cycloduction θ1 described below) is given with a certain precision by the application of the conventional measurement method using the iris shading pattern for the eye image when actually measuring.

Next, a blood vessel corresponding to the predetermined blood vessel selected in the reference state is specified from a plurality of end points of blood vessels in the vicinity of the boundary between the iris region and the sclera region which are detected in the eye image when actually measuring, through the use of the angle of cycloduction (first angle of cycloduction θ1 described below) calculated by the conventional measurement method which uses the iris shading pattern. After that, position information of the end point of the specified blood vessel (target end point Otgt described below) is acquired. In addition, the angle of cycloduction is then determined with higher precision, through the use of the position information of the end points of the blood vessels acquired in the reference state and in actual measurement, respectively.

(2) Processing by the Reference Information Acquisition Unit

In the cycloduction measurement method according to the present embodiment, the processing by the reference information acquisition unit 40 is performed before the actual measurement of cycloduction, and the reference information acquisition unit 40 acquires various reference information required for measurement of cycloduction. Meanwhile, the processing of acquiring various reference information performed by the reference information acquisition unit 40 differs from the processing when actually measuring cycloduction (for example, when actually measuring the health state of the subject).

In the present embodiment, first, the eyeball is photographed using the aforementioned two types of illumination (infrared LED 32 and blue LED 34) when acquiring reference information. At this time, the pupil region and the iris region are irradiated with infrared light, whereas the circumference of the blood vessel (sclera region) is irradiated with blue light.

Next, the reference information acquisition unit 40 analyzes the subject's eye image acquired in the reference state, and acquires information such as difference vector data fref of the iris shading pattern in the reference state, position information of the end point of the predetermined blood vessel (target end point Otgt0), ellipse parameters of the pupil (for example, information pertaining to the center point, the major axis value, the minor axis value of the pupil contour, inclination of the ellipse (rotational angle of major axis), and the like. Meanwhile, the meaning of the aforementioned information and a specific acquisition technique thereof will be described in detail below.

The reference information acquisition unit 40 then outputs the acquired various pieces of information to the memory device 18 or the auxiliary storage device 16, for example. When acquiring reference information, various reference information is acquired by the reference information acquisition unit 40 and stored in the memory device 18 or the auxiliary storage device 16, as described above. The position information of the end point (target end point Otgt0) of the predetermined blood vessel output from the reference information acquisition unit 40 are coordinates of an X-Y orthogonal coordinate system (see FIG. 3 described below) with the horizontal direction and the vertical direction of the eye image in the reference state being the X-axis direction and the Y-axis direction, respectively.

(3) Processing by the Iris Pattern Recognition Processing Unit

The iris pattern recognition processing unit 42 calculates the angle of cycloduction $\theta 1$ (hereinafter, referred to as first angle of cycloduction $\theta 1$) with a certain precision, on the basis of the iris shading pattern recognized in the eye image, photographed by the camera 30 when actually measuring cycloduction, of the same subject as the subject when acquiring reference information. Hereinafter, the processing by the iris pattern recognition processing unit 42 will be described in more detail.

Figure 3:
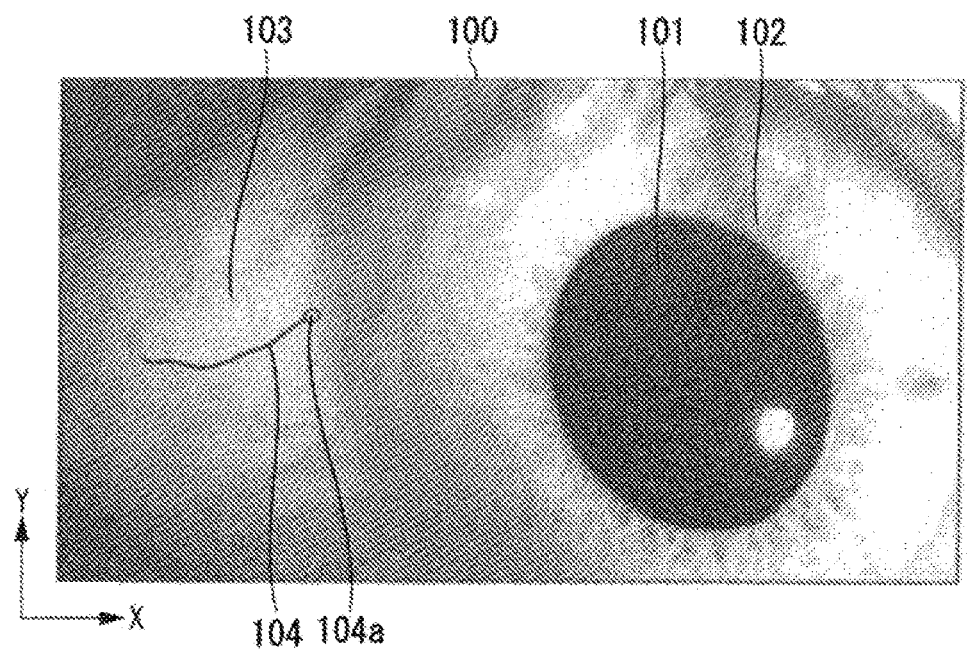
FIG. 3 illustrates the pupil region, the iris region, the sclera region, the conjunctival blood vessel, and an end point of the conjunctival blood vessel, in an eye image.

First, the iris pattern recognition processing unit 42 binarizes the eye image in accordance with pixel values, and thus extracts the pupil region in the eye image. FIG. 3 illustrates an exemplary eye image 100 photographed by the camera 30, as well as a pupil region 101, an iris region 102, sclera region 103, a blood vessel 104, and an end point 104a of the blood vessel 104 in the eye image 100. Since the contrast is the highest at the contour part of the pupil region 101, as illustrated in FIG. 3, the pupil region 101 and its contour (pupil contour) in the image can be easily extracted by binarizing the eye image 100.

Next, the iris pattern recognition processing unit 42 performs, for example, ellipse fitting processing on the extracted pupil contour and acquires the ellipse parameters (for example, coordinates of pupil center, the major axis value, the minor axis value, inclination of ellipse and the like) of the pupil contour (pupil ellipse) obtained by the processing. In addition, the iris pattern recognition processing unit 42 then outputs the ellipse parameters of the acquired pupil contour to the memory device 18 or the auxiliary storage device 16. Meanwhile, as illustrated in FIG. 3, the inclination of the ellipse included in the ellipse parameters is the inclination angle (counter-clockwise rotational angle with respect to the Y-axis) of the major axis with respect to the Y-axis (zero degree) of the ellipse exhibiting the pupil contour, when the horizontal direction and the vertical direction of the eye image 100 are defined as the X-axis direction and the Y-axis direction, respectively.

The procedure of the ellipse fitting processing is as follows. First, the iris pattern recognition processing unit 42 prepares an ellipse having, for example, predetermined ellipse parameters. Subsequently, the iris pattern recognition processing unit 42 overlays the ellipse on the pupil contour while changing the rotational angle (inclination of the major axis), the flatness, and the size of the ellipse. The iris pattern recognition processing unit 42 then searches for and extracts an ellipse for which the separation between the ellipse and the pupil contour is less than a predetermined range. At this time, various types of methods can be used as the method for extracting the ellipse, and for example, a method such as the least-squares method can be used.

Meanwhile, in the present embodiment, the ellipse parameters of the pupil contour acquired at the time of acquisition of reference information is acquired, in the same manner as the aforementioned method. At this time, the present embodiment may cause the reference information acquisition unit 40 to perform the aforementioned processing by the iris pattern recognition processing unit 42 and acquire the ellipse parameters of the pupil contour, or may cause the iris pattern recognition processing unit 42 to perform the aforementioned processing, and cause the reference information acquisition unit 40 to acquire the calculation result from the iris pattern recognition processing unit 42.

Next, the iris pattern recognition processing unit 42 recognizes the boundary line between the iris region 102 and the sclera region 103 on the basis of the binarized eye image 100, in the same manner as the case of the pupil contour, and performs the ellipse fitting processing on the boundary line. In addition, the iris pattern recognition processing unit 42 then outputs, to the memory device 18 or the auxiliary storage device 16, the ellipse parameters of the boundary line between the iris region 102 and the sclera region 103 (periphery of the iris region 102) obtained by the ellipse fitting processing.

Subsequently, the iris pattern recognition processing unit 42 sets a virtual ellipse at a position outside the pupil contour and inside the periphery of the iris region 102. Next, the iris pattern recognition processing unit 42 sets, for example, the center of the virtual ellipse as a center of rotation, and performs sampling of pixel values of pixels existing on the virtual ellipse for each predetermined angle $\theta s$ along the ellipse to thereby generate vector data f. FIG. 4 illustrates a state of sampling pixel values of pixels existing on a virtual ellipse E and generating the vector data f ($=( \ldots, Z1, Z2, Z3, Z4, \ldots )$). Meanwhile, each component $Zi$ ($i$ is an integer) of the vector data f is a pixel value of a corresponding sample point (pixel) on the virtual ellipse E.

It is preferable that the virtual ellipse E is precisely set in accordance with the subject's personal characteristics. More specifically, the virtual ellipse E is set to have a diameter slightly larger than the diameter (minor axis or major axis) of the pupil most widely opened by dark adaptation of the subject. For example, when the diameter (minor axis or major axis) of the pupil most widely opened is 7 mm, it sufficient that the diameter of the virtual ellipse E is set to about 7.5 mm. Meanwhile, in the present embodiment, it is assumed that ellipse parameters other than the diameter of the virtual ellipse E are similar to corresponding ellipse parameters of the pupil contour.

The reason for setting the virtual ellipse E in the manner described above is as follows. Since the contrast of the iris shading pattern is higher in an area close to the pupil, it is desirable to set the virtual ellipse E at a position as close to the pupil as possible to thereby extract the pixel value (generate the vector data f). However, it is necessary to prevent the virtual ellipse E from overlapping the pupil when the pupil is most widely opened. Therefore, it is preferable to set the diameter of the virtual ellipse E (minor axis or major axis) to a diameter slightly larger than the diameter of the subject's pupil most widely opened, as described above. Meanwhile, the present invention is not limited thereto and the virtual ellipse E may be set at substantially an intermediate position between the contour position of the pupil and the periphery position of the iris region 102.

Next, the iris pattern recognition processing unit 42 calculates the difference between the pixel value (each component $Zi$ of the vector data f) of each pixel included in the vector data f of the virtual ellipse E and the pixel value (adjacent component of the vector data f) of an adjacent pixel separated from the pixel by an angle $\theta s$ and generates the difference vector data fd.

Meanwhile, in the present embodiment, the difference vector data fref of the iris shading pattern acquired at the time of acquisition of reference information is also calculated in a manner similar to the aforementioned method. At this time, the present embodiment may cause the reference information acquisition unit 40 to perform the calculation processing by the iris pattern recognition processing unit 42 and acquire the difference vector data fref of the iris shading pattern in the reference state, or may cause the iris pattern recognition processing unit 42 to perform the calculation processing and cause the reference information acquisition unit 40 to acquire the calculation result from the iris pattern recognition processing unit 42.

Subsequently, the iris pattern recognition processing unit 42 calculates, a plurality of times, the mutual correlation function R(k) between the difference vector data fref of the iris shading pattern in the reference state and the difference vector data fd calculated when actually measuring cycloduction, while changing the parameter (variable) k (=0, 1, 2, ... ). Meanwhile, the mutual correlative function R(k) is expressed by the following formula (1).

[Expression 1]

$$R(k) = \Sigma \{f_{ref}(m) \cdot f_d(m+k)\} \quad (1)$$

In the above formula (1), the parameter "m" is an index of each component Zi of the vector data f, and the parameter "k" is a relative shift amount of the index of each component of the difference vector data fd from the difference vector data fref. In addition, total sum "Σ" in the above formula (1) is the total sum with regard to the parameter "m".

As indicated by the above formula (1), the mutual correlative function R(k) is a parameter resulting from multiplying each component of the difference vector data fref with each component of the difference vector data fd whose index is shifted by k steps from each component of the difference vector data fref, and summing up the results of multiplication. Therefore, the value of the mutual correlative function R(k) becomes largest when distribution of each component of the difference vector data fd whose index is shifted by k steps is closest to the distribution of the components of the difference vector data fref in the reference state.

In addition, the iris pattern recognition processing unit 42 specifies the value (kp) of the parameter k at which the mutual correlative function R(k) becomes largest, and calculates an angle (kp×θs) corresponding to the value (kp) of the specified parameter k, as a first angle of cycloduction θ1 (reference angle of cycloduction).

Figure 5A:
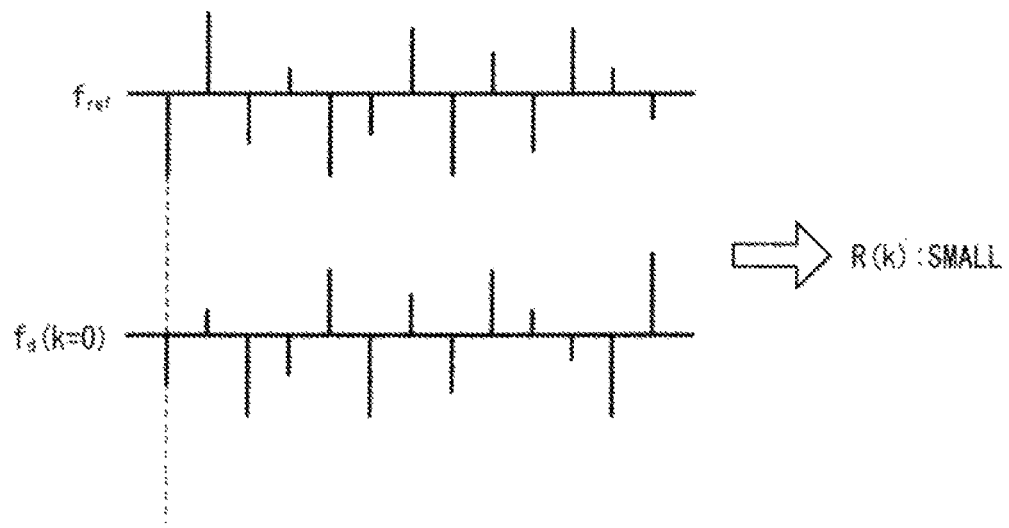
FIGS. 5A and 5B illustrate the relation between the distribution of the components of difference vector data fref in the reference state, the distribution of the components of the difference vector data fd when actually measuring cycloduction, and a mutual correlation function R(k)
Figure 5B:
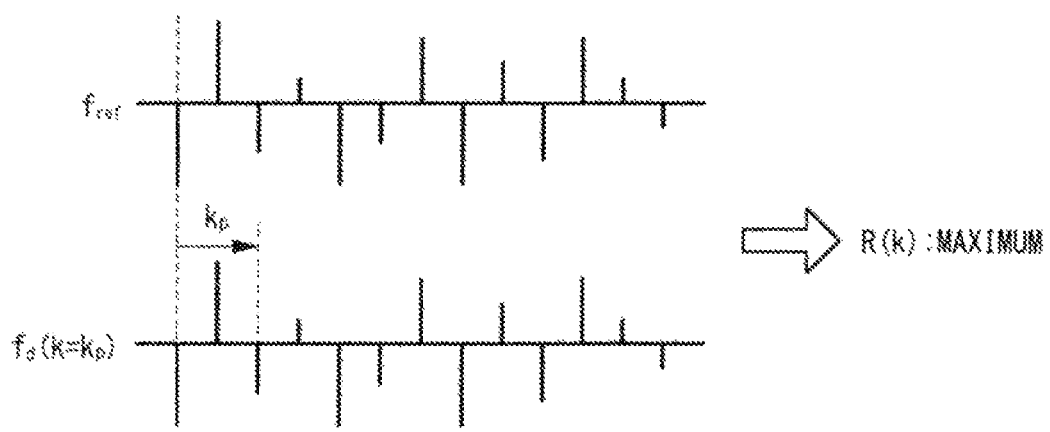

FIGS. 5A and 5B illustrate the relation between the distribution of each component of the difference vector data fref in the reference state, the distribution of each component of the difference vector data fd when actually measuring cycloduction, and the mutual correlation function R(k). The height of the bar graph (vertical axis) illustrated in each drawing indicates the pixel value Zi of each component of vector data, and the horizontal axis of the bar graph indicates the index m of each component. Meanwhile, FIG. 5A illustrates the relation between both difference vector data when the relative shift amount of the index of each component of the difference vector data fd from the difference vector data fref is zero (k=0). In addition, FIG. 5B illustrates the relation between both difference vector data when the relative shift amount of the index of each component of the difference vector data fd from the difference vector data fref is "kp".

As illustrated in FIG. SA, the distribution of each component of the difference vector data fd is different from the distribution of each component of the difference vector data fref when the relative shift amount of the index of each component of the difference vector data fd is zero (k=0), and thus the mutual correlation function R(k) decreases. When, on the other hand, the relative shift amount of the index of each component of the difference vector data fd is "kp", the distribution of each component of the difference vector data fd is the same as the distribution of each component of the difference vector data fref, and thus the mutual correlation function R(k) becomes the largest, as illustrated in FIG. 5B. Meanwhile, here, "shifting by k steps" of the index of each component of the vector data means shifting by k indices of each component to a predetermined direction (rightward in the example illustrated in FIG. 5B) along the direction of arrangement of each component, as illustrated in FIG. 5B.

The first angle of cycloduction θ1 (=kp×θs) acquired by the aforementioned method which uses the iris shading pattern expresses the angle of cycloduction with a certain accuracy. For example, it is known by experiments that, under a certain condition, the angle of cycloduction can be measured with a resolution of about 1 degree. However, the cycloduction measurement device 1 of the present embodiment performs a processing by the blood vessel position recognition unit 44 and a processing by the angle calculation unit 46 described below, in order to allow measurement of the angle of cycloduction with a still higher resolution (resolution of about several tenths of a degree).

(4) Processing by the Blood Vessel Position Recognition Unit

The blood vessel position recognition unit 44 recognizes the position of the blood vessel 104 in sclera region 103, and outputs information pertaining to the recognized position of the blood vessel 104 to, for example, the memory device 18 or the auxiliary storage device 16. The sclera region 103 is an area outside the iris region 102 recognized by the iris pattern recognition processing unit 42 in the eye image 100, as illustrated in FIG. 3. At this time, the blood vessel 104 to be recognized (specified) by the blood vessel position recognition unit 44 is a blood vessel corresponding to the predetermined blood vessel (hereinafter, referred to as corresponding blood vessel) selected by reference information acquisition unit 40 when acquiring reference information.

More specifically, the blood vessel position recognition unit 44 refers to the reference information stored in the memory device 18 or the auxiliary storage device 16, and acquires the position information of the end point of the corresponding blood vessel existing in the vicinity of the periphery of the iris region 102 (hereinafter, referred to as a "target end point") in the eye image 100 when actually measuring. In addition, the blood vessel position recognition unit 44 outputs the acquired position information (coordinate information) of the target end point of the corresponding blood vessel to, for example, the memory device 18 or the auxiliary storage device 16. Hereinafter, the processing by the blood vessel position recognition unit 44 will be described in more detail.

Figure 6:
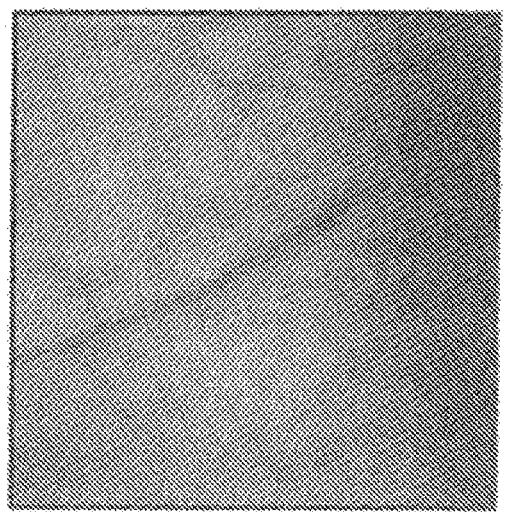
FIG. 6 is an exemplary original image of a search area acquired by a cycloduction measurement method according to the first embodiment.
Figure 7:
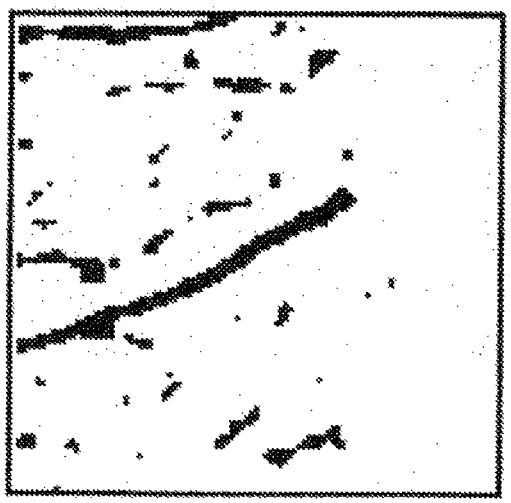
FIG. 7 is an exemplary image after performing binarization processing on the original image of the search area.
Figure 8:
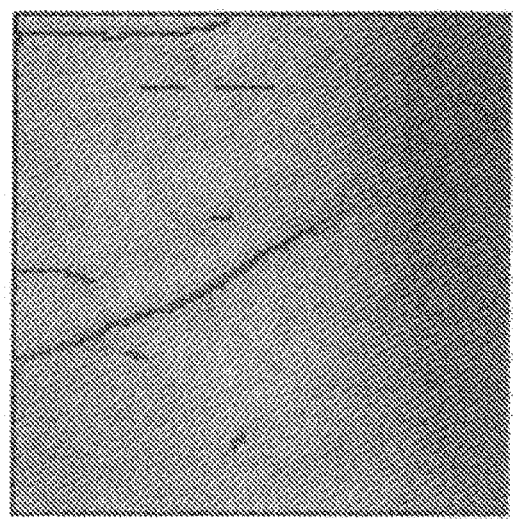
FIG. 8 is an exemplary image after performing noise removal processing according to Hilditch's thinning algorithm on the blood vessel part in the search area having the binarization processing performed therein.

First, the blood vessel position recognition unit 44 reads, from the memory device 18 or the auxiliary storage device 16, the position information (coordinate information) of the target end point Otgt0 of the predetermined blood vessel in the reference state preliminarily acquired by the reference information acquisition unit 40. Subsequently, the blood vessel position recognition unit 44 sets a search area for specifying the position of a corresponding blood vessel in the eye image 100 acquired when actually measuring, on the basis of the read position information of the target end point Otgt0 of the predetermined blood vessel in the reference state. Specifically, the blood vessel position recognition unit 44 sets a point, which is rotated the target end point Otgt0 of the predetermined blood vessel in the reference state by the first angle of cycloduction θ1, as the reference end point Oref (assumed end point position), and sets, in the eye image 100, a search area having a predetermined shape (in the present embodiment, square shape as illustrated in FIGS. 6 to 8 described below), with the reference endpoint Oref as a center.

Next, the blood vessel position recognition unit 44 performs, for example, smoothing processing on an image in the search area to thereby remove noise. Subsequently, the blood vessel position recognition unit 44 performs binarization processing, in accordance with the pixel value, on the image subjected to the smoothing processing in the search area, and recognizes a gathering portion of pixels having lower pixel values as a blood vessel. At this time, a plurality of blood vessels is recognized in the search area (see FIG. 7 described below).

Furthermore, the blood vessel position recognition unit 44 performs noise removal processing by applying Hilditch's thinning algorithm to the gathering portion of pixels recognized to be a blood vessel. Subsequently, the blood vessel position recognition unit 44 measures the length of the blood vessel by performing depth-first search for the thin line part. The blood vessel position recognition unit 44 then extracts, from among the plurality of blood vessels recognized, only the blood vessels whose length is equal to or larger than a predetermined value.

In Hilditch's thinning method, a 3×3 window (pixel area) referring to a pixel of interest in the search area and eight peripheral pixels thereof is assumed to be a basic processing unit of the noise removal processing. In addition, the blood vessel position recognition unit 44 performs the thinning processing by setting each of the pixels as the pixel of interest and performing noise removal, while raster-scanning the entire image data of the search area.

Specifically, the blood vessel position recognition unit 44 first determines whether or not the pixel of interest satisfies the predefined deletion condition of the thinning in the 3×3 window. When the pixel of interest satisfies the deletion condition, the blood vessel position recognition unit 44 deletes the pixel of interest, that is, replaces the pictorial pixel (pixel in the blood vessel area) with a background pixel (pixel in the sclera region). On the other hand, when the pixel of interest does not satisfy the deletion condition, the blood vessel position recognition unit 44 selects the next pixel as a pixel of interest in order of raster-scanning and performs the determination processing of the pixel of interest and the replacement processing of the pictorial pixel, in a new 3×3 window.

In the noise removal processing using Hilditch's thinning method, the blood vessel position recognition unit 44 repeats the aforementioned series of processing for all of the pixels in the search area. Subsequently, the blood vessel position recognition unit 44 repeats the aforementioned series of processing while raster-scanning the search area until there is no pixel to be deleted in a single cycle of raster scanning. In addition, the blood vessel position recognition unit 44 then terminates the noise removal processing using Hilditch's thinning method when there is no pixel to be deleted in a single cycle of raster scanning.

FIGS. 6 to 8 respectively illustrate examples of the original image of the search area of the aforementioned corresponding blood vessel, an image of the search area after being binarized, and an image of the search area after applying Hilditch's thinning algorithm and performing noise removal.

Figure 9:
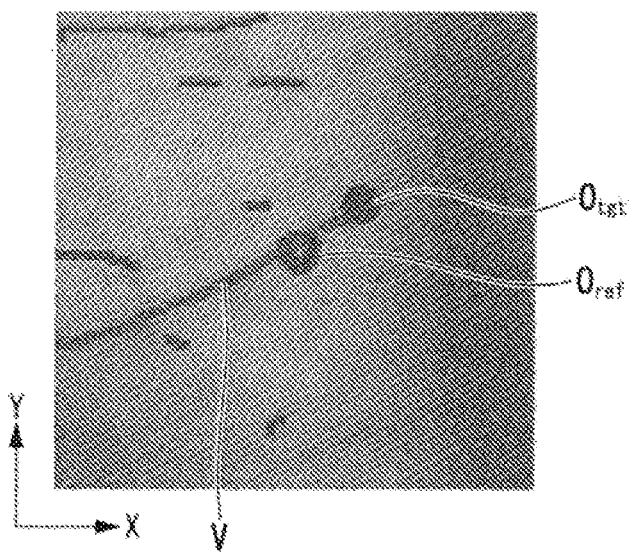
FIG. 9 illustrates the relation between the reference end point Oref of the conjunctival blood vessel and the target end point Otgt of the conjunctival blood vessel V selected when actually measuring.

After the noise removal processing using Hilditch's thinning algorithm, the blood vessel position recognition unit 44 specifies the position of the target end point of each extracted blood vessel, on the basis of the noise-removed image data in the search area. Subsequently, the blood vessel position recognition unit 44 selects, from the target end points of the plurality of blood vessels being specified, the target end point closest to the reference end point Oref, and sets the target end point as the target end point Otgt of the corresponding blood vessel in the eye image 100 when actually measuring. FIG. 9 illustrates the relation between the reference end point Oref at center of the search area and the target end point Otgt of the corresponding blood vessel V recognized (specified) by the blood vessel position recognition unit 44.

The blood vessel position recognition unit 44 then outputs, to the memory device 18 or the auxiliary storage device 16, for example, the position information (a first information pertaining to the position of the predetermined blood vessel) of the target end point Otgt of the specified corresponding blood vessel V. Here, the position information of the target end point Otgt of the corresponding blood vessel V output from the blood vessel position recognition unit 44 are coordinates of an X-Y orthogonal coordinate system (see FIGS. 3 and 9) with the horizontal direction and the vertical direction of the eye image 100 when actually measuring (search area) being the X-axis direction and the Y-axis direction, respectively.

In the present embodiment, the target end point Otgt0 of the predetermined blood vessel selected in the reference state is acquired as follows. First, a predetermined search area is set in the vicinity of the periphery of the iris region. Subsequently, the aforementioned series of processing from the binirization processing to the noise removal processing using Hilditch's thinning method performed by the blood vessel position recognition unit 44 is performed on the image data in the set predetermined search area, whereby end points of a plurality of blood vessels in the search area are extracted. The target end point Otgt0 of the predetermined blood vessel in the reference state is then selected from the plurality of extracted end points of the blood vessels. These processing may be performed by the reference information acquisition unit 40, or may be performed by the blood vessel position recognition unit 44 and thus the reference information acquisition unit 40 acquires the calculation result from the blood vessel position recognition unit 44.

In addition, the setting position, size, or the like of the search area when selecting the predetermined blood vessel at the time of acquisition of reference information may be set in an arbitrary manner. In addition, the criterion of selecting the target end point Otgt0 of the predetermined blood vessel from the plurality of extracted end points of the blood vessels in the search area may also be arbitrary.

However, in the present embodiment, it is preferable to select a blood vessel whose end point contacts the periphery of the iris region of the eyeball as the predetermined blood vessel. It is also preferable to select a blood vessel whose Y-axis coordinate of the end point of the blood vessel is closer (more preferably identical) to the Y-axis coordinate of the pupil center as the predetermined blood vessel. Selection of the predetermined blood vessel in this manner may prevent the measurement from being blocked by the eyelash, or interfered by eyelid movement or movement of line of sight, for example, (raising the possibility of an end point of a blood vessel appearing in the eye image 100), whereby tracking precision of the blood vessel (precision of recognizing (specifying) the target end point Otgt of the corresponding blood vessel) can be raised and the angle of cycloduction can be measured more reliably with higher precision. For a similar reason, it is preferable to set the search area so that the search area in the reference state is in the vicinity of the periphery of the iris region, and a Y-axis coordinate of the center point of the search area is closer (preferably identical) to the Y-axis coordinate of the pupil center.

(5) Processing by the Angle Calculation Unit

The angle calculation unit 46 calculates the angle of cycloduction θ, on the basis of the position information of the target end point Otgt0 of the predetermined blood vessel selected in the reference state and the position information of the target end point Otgt of the corresponding blood vessel (blood vessel corresponding to the predetermined blood vessel) specified (recognized) when actually measuring cycloduction. Specifically, the angle of cycloduction θ is obtained as follows.

First, in the present embodiment, an ellipsoidal coordinate system (ellipsoidal polar coordinate system) is set along the pupil contour (pupil ellipse). Specifically, there is set an ellipsoidal coordinate system (w, h, θp) which expresses position coordinates of a target end point of a blood vessel by a coordinate w along the minor axis (minor axis value) and a coordinate h (major axis value) along the major axis, passing through the pupil center P (ellipse center) of the pupil contour, and a counter-clockwise rotational angle coordinate Sp with the inclination of the major axis of the ellipse being zero degree (reference).

Therefore, there is set to be (Ixtgt0, Iytgt0), the coordinates (a second information pertaining to the position of the predetermined blood vessel) of the target end point Otgt0 of the predetermined blood vessel acquired at the time of acquisition of reference information in the X-Y orthogonal coordinate system, and set to be (xtgt00, ytgt00), the coordinates of the pupil center P in the reference state in the X-Y orthogonal coordinate system. In addition, there is set to be atgt0, the minor axis value of the pupil contour (coordinate of the pupil contour along the minor axis in the ellipsoidal coordinate system), set to be btgt0, the major axis value of the pupil contour (coordinate of the pupil contour along the major axis in the ellipsoidal coordinate system), and set to be φtgt0, the inclination of the major axis direction in the ellipsoidal coordinate system against the Y-axis direction in the X-Y orthogonal coordinate system, in the reference state. Furthermore, there is set to be θtgt0, the rotational angle coordinate θp of the target end point Otgt0 of the predetermined blood vessel in the ellipsoidal coordinate system, set to be wtgt0, the coordinate w along the minor axis, and set to be htgt0, the coordinate h along the major axis.

Meanwhile, among the various parameters in the reference state, parameters other than the rotational angle coordinate θtgt0, the minor axis coordinate wtgt0, and the major axis coordinate htgt0 of the target end point Otgt0 in the ellipsoidal coordinate system are preliminarily acquired by the reference information acquisition unit 40 at the time of acquisition of reference information, and are stored in, for example, the memory device 18 or the auxiliary storage device 16.

In addition, the relational expression of these parameters in the reference state is then given by the following formulae (2) (3) and (4). Meanwhile, the following formulae (2) (3) and (4) are an equation system for converting coordinates (w, h, θp) in the ellipsoidal coordinate system into coordinates (x, y) in the X-Y orthogonal coordinate system. Therefore, the angle calculation unit 46 can calculate the rotational angle coordinate θtgt0 of the target end point Otgt0 of the predetermined blood vessel selected in the reference state by back-calculating the equation system of the following formulae (2) (3) and (4).

[Expression 2]

$$Ix_{tgt0} = x_{tgt0} + w_{tgt0}\cos(\phi_{tgt0})\cos(\theta_{tgt0}) - h_{tgt0}\sin(\phi_{tgt0})\sin(\theta_{tgt0}) \quad (2)$$

$$Iy_{tgt0} = y_{tgt0} + w_{tgt0}\sin(\phi_{tgt0})\cos(\theta_{tgt0}) - h_{tgt0}\cos(\phi_{tgt0})\sin(\theta_{tgt0}) \quad (3)$$

$$w_{tgt0} = \frac{a_{tgt0}}{b_{tgt0}} h_{tgt0} \quad (4)$$

On the other hand, there is set to be (Ixtgt, Iytgt), the coordinates of the target end point Otgt of the corresponding blood vessel specified when actually measuring cycloduction (a first information pertaining to the position of the predetermined blood vessel) in the X-Y orthogonal coordinate system, and set to be (xtgt0, ytgt0), the coordinates of the pupil center P when actually measuring in the X-Y orthogonal coordinate system. In addition, there is set to be atgt, the minor axis value of the pupil contour, set to be φtgt, the major axis value of the pupil contour, and set to be (tgt, the inclination of the major axis direction in the ellipsoidal coordinate system against the Y-axis direction in the X-Y orthogonal coordinate system, when actually measuring. Furthermore, there is set to be θtgt, the rotational angle coordinate θp of the target end point Otgt of the corresponding blood vessel in the ellipsoidal coordinate system, set to be wtgt set to be the coordinate w along the minor axis, and set to be htgt, the coordinate h along the major axis.

Meanwhile, among the various parameters when actually measuring, parameters other than the rotational angle coordinate θtgt, the minor axis coordinate wtgt, and the major axis coordinate htgt of the target end point Otgt in the ellipsoidal coordinate system is preliminarily calculated by the processing of the iris pattern recognition processing unit 42 and the blood vessel position recognition unit 44, and is stored in the memory device 18 or the auxiliary storage device 16, for example.

In addition, the relational expression of these parameters when actually measuring cycloduction is given by the following formulae (5) (6) and (7). Furthermore, the angle calculation unit 46 then can calculate the rotational angle coordinate θtgt of the target end point Otgt of the corresponding blood vessel specified when actually measuring cycloduction by back-calculating the equation system of the following formulae (5) (6) and (7).

[Expression 3]

$$Ix_{tgt} = x_{tgt} + w_{tgt0}\cos(\phi_{tgt0})\cos(\theta_{tgt0}) - h_{tgt}\sin(\phi_{tgt0})\sin(\theta_{tgt0}) \quad (5)$$

$$Iy_{tgt} = y_{tgt} + w_{tgt0}\sin(\phi_{tgt0})\cos(\theta_{tgt0}) - h_{tgt}\cos(\phi_{tgt0})\sin(\theta_{tgt0}) \quad (6)$$

$$w_{tgt} = \frac{a_{tgt}}{b_{tgt}} h_{tgt} \quad (7)$$

Subsequently, the angle calculation unit 46 calculates the angle of cycloduction θ by subtracting the rotational angle coordinate θtgt0 of the target end point Otgt0 of the predetermined blood vessel in the reference state from the rotational angle coordinate θtgt of the target end point Otgt of the corresponding blood vessel which has been calculated as described above. Namely, the angle calculation unit 46 calculates the angle of cycloduction θ on the basis of the following formula (8).

[Expression 4]

$$\theta = \theta_{tgt} - \theta_{tgt0} \quad (8)$$

Figure 10:
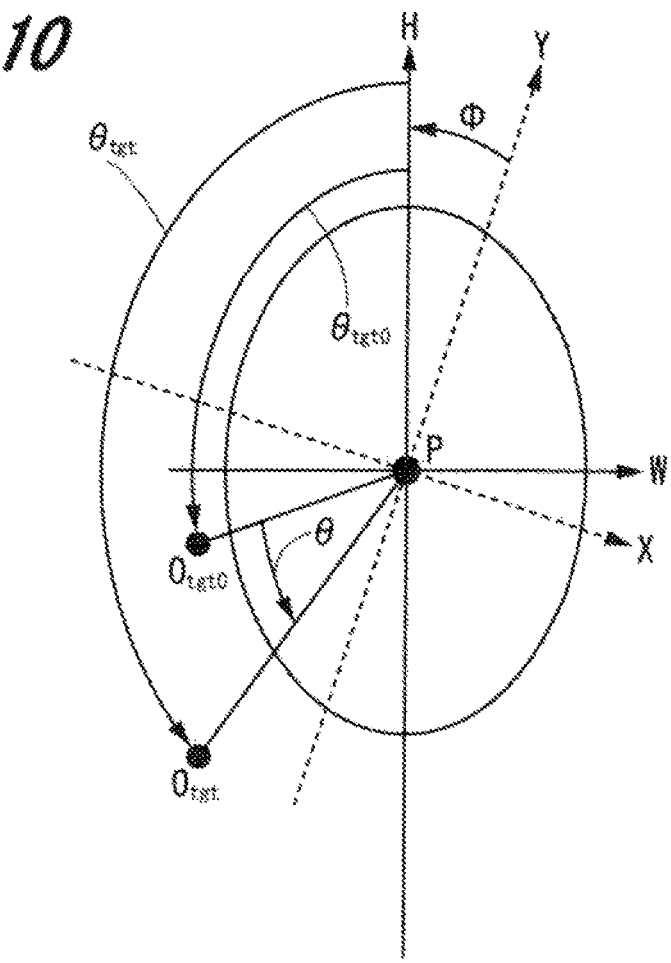
FIG. 10 illustrates the relation between the rotational angle coordinate θtgt0 of the target end point Otgt0 of the conjunctival blood vessel in the reference state, the rotational angle coordinate θtgt of the target end point Otgt of the conjunctival blood vessel selected when actually measuring, and the angle of cycloduction θ.

FIG. 10 illustrates the relation between the ellipsoidal coordinate system and the X-Y orthogonal coordinate system which are set when calculating the angle of cycloduction θ, and the relation between the rotational angle coordinate θtgt0 of the target end point Otgt0 of the predetermined blood vessel selected in the reference state, the rotational angle coordinate θtgt of the target end point Otgt of the corresponding blood vessel specified when actually measuring, and the angle of cycloduction θ. For simplification of the explanation, FIG. 10 illustrates the size and flatness of the virtual ellipse passing through the target end point Otgt0 acquired in the reference state (at the time of acquisition of reference information) so as to be the same as the size and flatness of the virtual ellipse passing through the target end point Otgt acquired when actually measuring cycloduction.

[Flow Chart of Cycloduction Measurement Processing]

Figure 11:
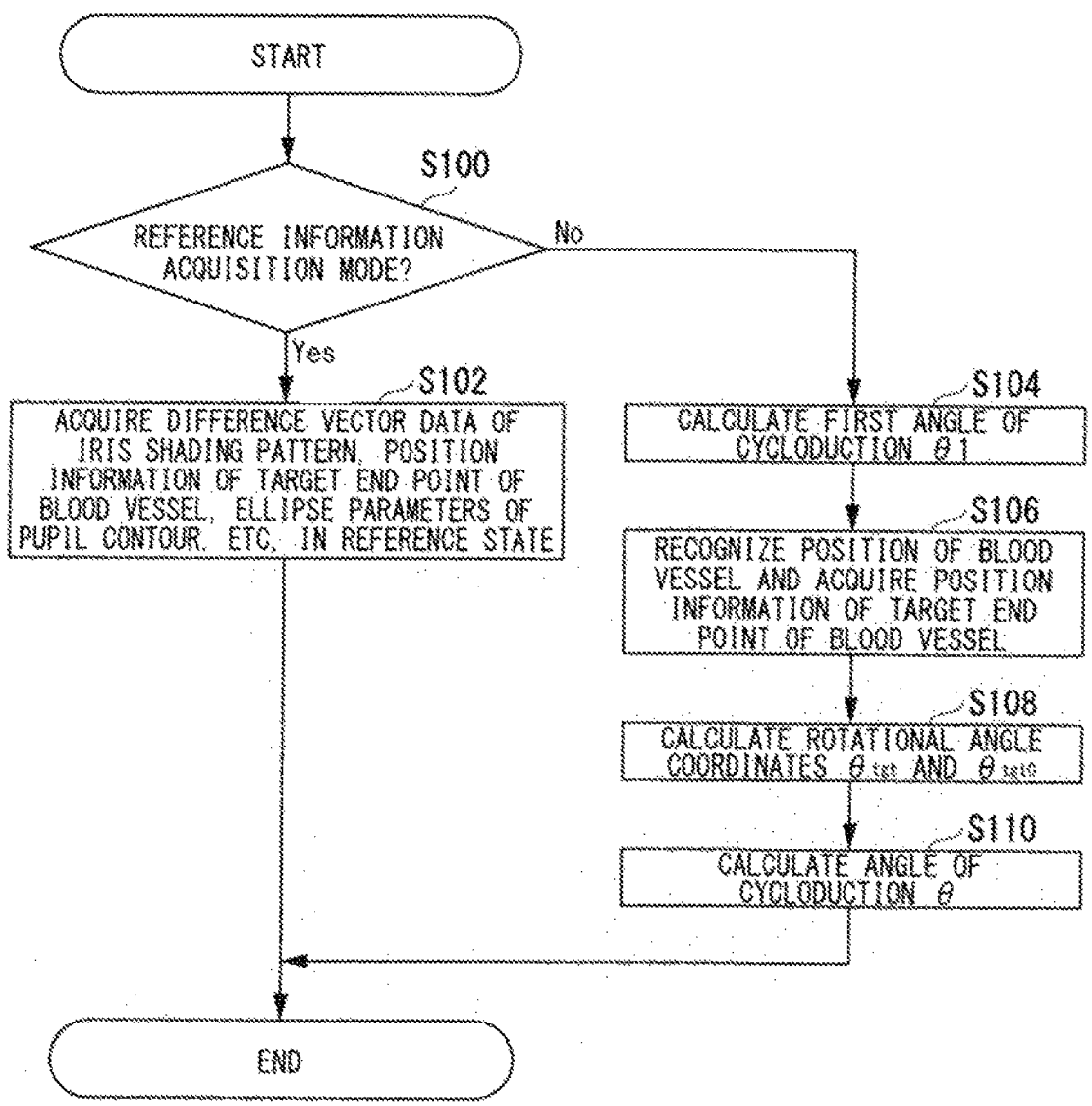
FIG. 11 is a flow chart illustrating a processing procedure of the cycloduction measurement method according to the first embodiment.

Next, a specific processing procedure when performing cycloduction measurement by the cycloduction measurement device 1 of the present embodiment will be described, referring to FIG. 11. FIG. 11 is a flow chart illustrating a processing procedure of the cycloduction measurement method performed by the cycloduction measurement device 1 of the present embodiment.

First, the cycloduction measurement device 1 determines whether or not the current measurement mode is the reference information acquisition mode (S100). The determination processing is performed as follows, for example. First, there is preliminarily prepared a control flag indicating whether or not the current measurement mode is the reference information acquisition mode. Let us consider a case where a certain operation is performed on the cycloduction measurement device 1 by an operator, for example, and the control flag turns ON when the reference information acquisition mode is set as the measurement mode. In such case, the cycloduction measurement device 1 determines whether or not the current measurement mode is the reference information acquisition mode by discriminating the ON/OFF state of the control flag at S100. The timing of performing the determination processing of S100 may be, for example, the time point when the reference information acquisition mode is set by the operator or may be the time point when the first image is input.

When the current measurement mode is the reference information acquisition mode at S100, the result of determination at S100 is Yes. In such case, the cycloduction measurement device 1 analyzes the subject's eye image acquired in the reference state, and acquires reference information such as the difference vector data fref of the iris shading pattern in the reference state, the position information of the target end point Otgt0 of the predetermined blood vessel, the ellipse parameters of the pupil contour in the reference state (center position of the pupil, the minor axis value and the major axis value of the ellipse, inclination (rotational angle) of the major axis, etc.) (S102). The cycloduction measurement device 1 then terminates the cycloduction measurement processing after having output the acquired reference information to the memory device 18 or the auxiliary storage device 16. In the processing of S102, the cycloduction measurement device 1 acquires the aforementioned various reference information in the reference state according to the aforementioned processing operation of the reference information acquisition unit 40.

When, on the other hand, the current measurement mode is not the reference information acquisition mode at S100, in other words, the current measurement mode is the actual cycloduction measurement mode, the result of determination at S100 is No. In such case, the cycloduction measurement device 1 analyzes the eye image when actually measuring acquired from the same subject as when acquiring reference information, and calculates the first angle of cycloduction θ1 on the basis of the iris shading pattern recognized in the eye image (S104). In the processing of S104, the cycloduction measurement device 1 calculates the first angle of cycloduction θ1 according to the aforementioned processing operation of the iris pattern recognition processing unit 42.

Subsequently, the cycloduction measurement device 1 recognizes the positions of a plurality of blood vessels in the sclera region in the eye image, and specifies a corresponding blood vessel (blood vessel corresponding to the predetermined blood vessel selected at the time of acquisition of reference information) from the plurality of blood vessels. The cycloduction measurement device 1 then acquires the position information (information pertaining to the position of the blood vessel) of the target end point Otgt (end of the blood vessel at the pupil side) of the corresponding blood vessel (S106). In the processing of S106, the cycloduction measurement device 1 acquires the position information of the target end point Otgt according to the aforementioned processing operation of the blood vessel position recognition unit 44. In addition, at S106, the cycloduction measurement device 1 acquires the ellipse parameters of the pupil contour when actually measuring.

Subsequently, the cycloduction measurement device 1 calculates the rotational angle coordinate θtgt of the target end point Otgt of the corresponding blood vessel in the ellipsoidal coordinate system using the position information of the target end point Otgt of the corresponding blood vessel when actually measuring acquired at S106 and the ellipse parameters of the pupil contour, and further calculates the rotational angle coordinate θtgt0 of the target end point Otgt0 of the predetermined blood vessel in the ellipsoidal coordinate system using the reference information acquired at S102 for the same subject as the subject when actually measuring (S108). The cycloduction measurement device 1 then subtracts the rotational angle coordinate θtgt0 from the rotational angle coordinate θtgt calculated at S108, and calculates the angle of cycloduction θ (S110). In the processing of S108 and S110, the cycloduction measurement device 1 calculates the angle of cycloduction θ according to the aforementioned processing operation of the angle calculation unit 46.

In the present embodiment, cycloduction measurement is performed in the manner described above. In the present embodiment, the aforementioned cycloduction measurement processing may be realized by implementing a corresponding cycloduction measurement program in the cycloduction measurement device 1 and executing the cycloduction measurement program by the CPU 10.

The aforementioned cycloduction measurement technique of the present embodiment calculates the angle of cycloduction θ on the basis of the position information of the blood vessel end (target end point of the conjunctival blood vessel) having a higher contrast to the periphery and being not much affected by pupil contraction, and therefore can measure cycloduction with higher precision. Specifically, according to the present embodiment, the angle of cycloduction θ can be measured with a resolution of about several tenths of a degree and cycloduction can be measured with higher precision than the conventional method (method which uses the iris shading pattern).

Additionally, in the present embodiment, the angle of cycloduction θ is calculated on the basis of the position information of the blood vessel end (target end point) located in the vicinity of the periphery of an iris region, as described above. In such case, the blood vessel end is located at a position which is closest to the pupil in the sclera region, whereby the effect on detection of the blood vessel end (target end point) by eyelid movement or the like is minimized. Therefore, using the position information of the blood vessel end (target end point) located in the vicinity of the periphery of the iris region allows cycloduction to be measured with higher precision, as the present embodiment.

Additionally, in the present embodiment, the angle of cycloduction (the first angle of cycloduction θ1) is first calculated with a certain precision by the cycloduction measurement method which uses the iris shading pattern when measuring the angle of cycloduction θ as described above, and the target end point Otgt of the blood vessel (corresponding blood vessel) to be detected is specified using the angle of cycloduction. Using such a method allows the target end point Otgt of the corresponding blood vessel to be specified faster when actually measuring, whereby the angle of cycloduction θ can be calculated with a higher speed. Furthermore, using such a method realizes low-cost cycloduction measurement, and also allows measurement of the angle of cycloduction θ with high precision and a high resolution even when the pupil diameter varies.

<2. Second embodiment>

Generally, substances such as an eyelash, dust, and fine powder of cosmetics may easily fall in the eye, and existence of such substances in the vicinity of the periphery of the iris region may generate a noise source which degrades the measurement precision of cycloduction in the present invention. Therefore, in the present invention, in order to measure cycloduction motion more accurately, it is preferable to automatically select (specify), at the measurement, a blood vessel end which is not blocked by a substance (noise) such as an eyelash, from end points of a plurality of conjunctival blood vessels (hereinafter, referred to as a blood vessel end, for short) existing in the vicinity of the periphery (contour) of the iris region. In the second embodiment, an example of the cycloduction measurement device and the cycloduction measurement method, capable of performing such processing will be described.

Meanwhile, the hardware configuration and the functional configuration of the cycloduction measurement device 1 according to the present embodiment are similar to the first embodiment (see FIGS. 1 and 2), and thus the description of these configurations is omitted below.

[Cycloduction Measurement Method]

(1) Outline of the Cycloduction Measurement Method

The cycloduction measurement method according to the present embodiment will be specifically described while describing various processing performed in the functional blocks illustrated in FIG. 2, but before that, the cycloduction measurement method according to the present embodiment will be outlined.

In the cycloduction measurement method according to the present embodiment, first, the periphery of the iris region is recognized, and a plurality of blood vessel ends existing in the vicinity of the periphery are automatically detected. Subsequently, a pattern matching processing is performed on a predetermined image area (matching area described below) including each of the detected blood vessel ends, using corresponding reference information (template video image described below). In addition, a blood vessel end with the smallest noise (target end point of the blood vessel) is automatically specified from the plurality of blood vessel ends, on the basis of the matching result (degree of similarity described below). The use of such a method can further enhance the measurement precision of the angle of cycloduction θ.

In addition, in the same manner as the first embodiment, the present embodiment makes use of both the aforementioned automatic selection method of the blood vessel end, and the conventional cycloduction measurement method using the iris shading pattern described in the first embodiment. Accordingly, high-speed and low-cost cycloduction measurement becomes possible, and measurement of the angle of cycloduction with high precision and high resolution even when the pupil diameter changes is possible.

(2) Processing by the Reference Information Acquisition Unit

When acquiring reference information, first, the eyeball is photographed using two types of illumination (infrared LED 32 and blue LED 34) in the same manner as the first embodiment. At this time, the pupil and the iris regions are irradiated with infrared light, whereas the circumference of the blood vessel (sclera region) is irradiated with blue light.

In the present embodiment, a video image is used as the eye image. Additionally, in the present embodiment, the infrared LED 32 is temporarily turned OFF in the course of capturing the video image. This is because of raising the contrast between the iris region 102 and the sclera region 103 in the determination processing of the contour of the iris region 102 described below.

Figure 12:
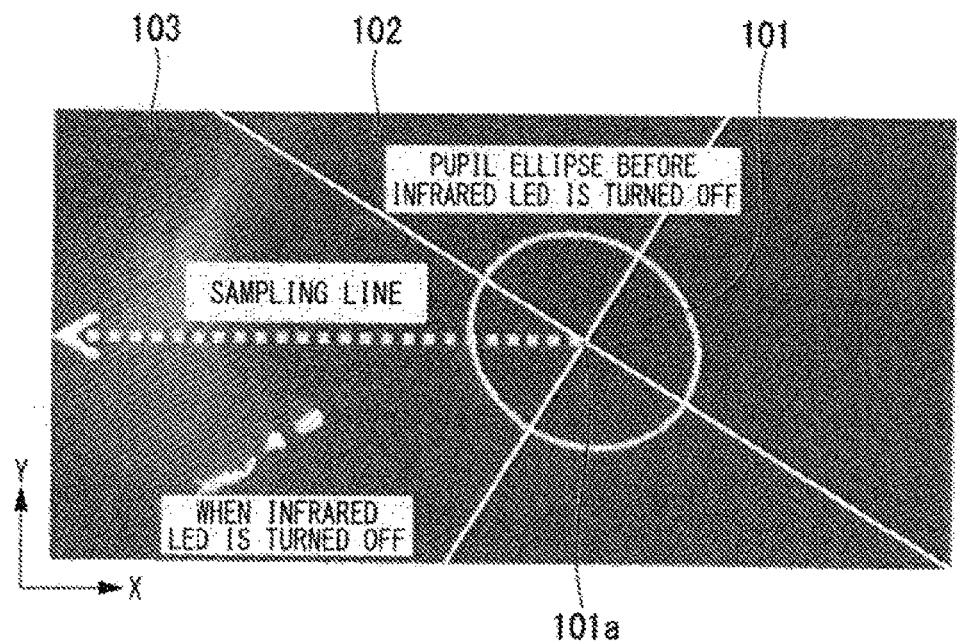
FIG. 12 is an explanatory diagram of processing of determining the boundary between the iris region and the sclera region, on the basis of the cycloduction measurement method according to the second embodiment of the present invention.
Figure 13:
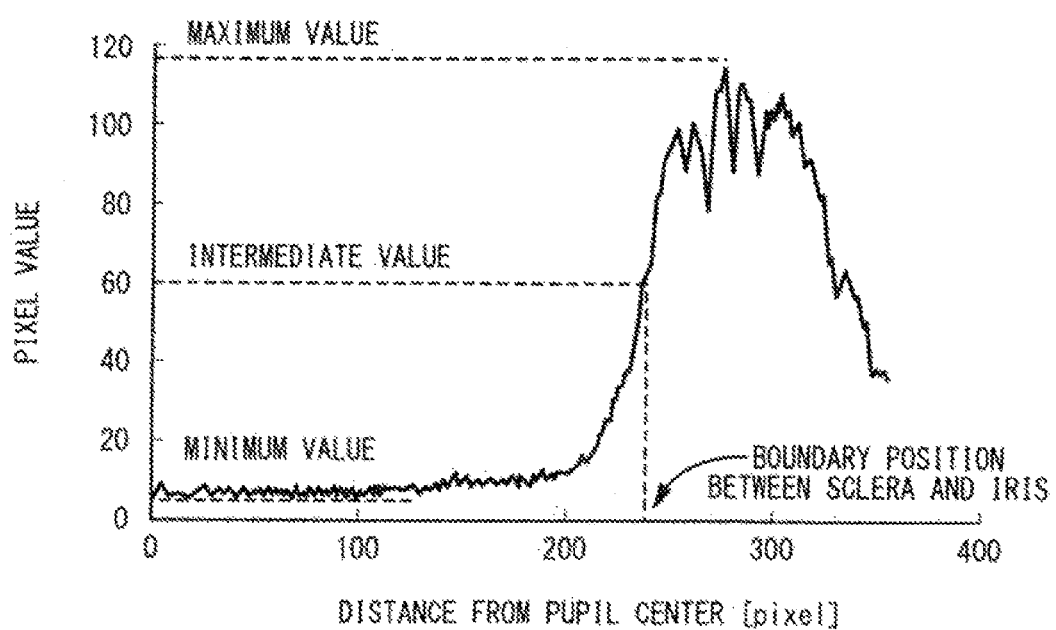
FIG. 13 is an explanatory diagram of processing of determining a boundary between the iris region and the sclera region, on the basis of the cycloduction measurement method according to the second embodiment of the present invention.

First, the reference information acquisition unit 40 analyzes the subject's eye image acquired in the reference state, recognizes the boundary between the iris region 102 and the sclera region 103 (periphery of the iris region), and determines the coordinates of the boundary. FIGS. 12 and 13 are explanatory diagrams of the method of determining the coordinates of the boundary between the iris region 102 and the sclera region 103 using the eye image.

In the determination method of the boundary between the iris region 102 and the sclera region 103, the reference information acquisition unit 40 first acquires the ellipsoidal coordinate system along the contour of the pupil from the eye image. To provide a more specific description of the processing, the pupil region 101 has a lower pixel value than other regions, as described in the aforementioned first embodiment, and thus the reference information acquisition unit 40 binarizes the original image of the eyeball and extracts a region with a low pixel value as the pupil region 101. Subsequently, the reference information acquisition unit 40 performs ellipse approximation (ellipse fitting processing) on the contour of the extracted pupil region 101 by using the least-squares method.

Accordingly, the reference information acquisition unit 40 acquires the ellipse parameters (for example, information pertaining to the center point of the pupil contour, the major axis value, the minor axis value, the rotational angle of the major axis, etc.) of the pupil contour (pupil ellipse). The reference information acquisition unit 40 then sets, from the ellipse parameters acquired by ellipse approximation, an ellipsoidal coordinate system with the major axis of the ellipse being the reference (zero degree) of the rotational direction coordinate.

The coordinates in the ellipsoidal coordinate system are expressed by the coordinate h (major axis value) in the major axis direction of the ellipse, the coordinate w (minor axis value) in the minor axis direction, and the rotational angle coordinate θp in the counter-clockwise direction against the major axis, with the coordinates (x0, y0) of the center 101*a* of the pupil contour in the X-Y orthogonal coordinate system of the camera video image (eye image) being the origin. In the present embodiment, inclination of the major axis of the ellipsoidal coordinate system against the Y-axis (axis in the vertical direction of the eye image) of the X-Y orthogonal coordinate system of the camera video image is denoted as φ.

The relation between arbitrary coordinates (w, h, θp) in the ellipsoidal coordinate system and coordinates (x, y) of in the X-Y coordinate system corresponding thereto is expressed in the following formula (9). The following formula (9) is an equation system for converting coordinates (w, h, θp) in the ellipsoidal coordinate system into coordinates (x, y) in the X-Y orthogonal coordinate system. "a" in the following formula (9) is a minor axis value of the pupil contour (coordinate along the minor axis direction of the pupil contour in the ellipsoidal coordinate system), and "b" is a major axis value of the pupil contour (coordinate along the major axis direction of the pupil contour in the ellipsoidal coordinate system).

[Expression 5]

$$\begin{cases} x = x_0 + w\cos(\phi)\cos(\theta p) - h\sin(\phi)\sin(\theta p) \\ y = y_0 + w\sin(\phi)\cos(\theta p) + h\cos(\phi)\sin(\theta p) \\ w = \frac{a}{b}h \end{cases} \quad (9)$$

In the present embodiment, the reference information acquisition unit 40 calculates the difference vector data of the iris shading pattern in the reference state after having acquired the ellipse parameters of the pupil contour, similarly to the aforementioned first embodiment.

Next, the reference information acquisition unit 40 determines the contour of the iris region 102. In the processing, the reference information acquisition unit 40 first acquires an eye image when the infrared LED 32 is turned OFF. In addition, the reference information acquisition unit 40 calculates the coordinates of the center 101*a* of the pupil contour through the use of an eye image one frame prior to that when the infrared LED 32 is turned OFF. As is apparent from the above, at least two frames of eye images, i.e., eye images before and after the infrared LED 32 is turned OFF are required in the present embodiment.

In the present embodiment, an eye image preceding the image acquired when the infrared LED 32 is turned OFF by two or more frames may be used as the eye image for calculating the coordinates of the center 101*a* of the pupil contour. However, in order to perform tracking of the blood vessel more reliably for ocular motion including movement of line of sight and cycloduction, it is preferable that the interval is short between the eye image before the infrared LED 32 is turned OFF used to calculate the coordinates of the center 101*a* of the pupil contour and the eye image when the infrared LED 32 is turned OFF.

Subsequently, the reference information acquisition unit 40 performs, in the eye image when the infrared LED 32 is turned OFF, sampling of pixel values of pixels along a direction (X-axis direction in the example of FIG. 12) toward the sclera region 103 from the center 101*a* of the pupil region 101 preliminarily calculated from the eye image before the infrared LED 32 is turned OFF, as illustrated in the dashed arrow in the FIG. 12.

FIG. 13 illustrates the sampling result of pixel values. The horizontal axis of the characteristics illustrated in FIG. 13 indicates the distance from the pupil center 101*a* of the sample point (pixel) on the sampling line (dashed arrow) in FIG. 12, and the vertical axis indicates the pixel values.

Subsequently, the reference information acquisition unit 40 sets the intermediate value between the minimum and the maximum of the pixel values acquired from the characteristics illustrated in FIG. 13 as the threshold for determining the boundary position between the iris region 102 and the sclera region 103. The reference information acquisition unit 40 then refers to the pixel values of sample points (pixels) sequentially outward from the pupil center 101*a* along the direction of the dashed arrow in FIG. 12, and acquires the pixel coordinates on which the pixel values exceeds the threshold as the boundary coordinates between the iris region 102 and the sclera region 103 (hereinafter, referred to as the sclera-iris boundary coordinates) on the sampling line.

Subsequently, the reference information acquisition unit 40 determines an elliptic orbit (periphery of iris region) for determining the detection range of the blood vessel end, using the sclera-iris boundary coordinates acquired as described above, and the above formula (9).

Specifically, the reference information acquisition unit 40 first calculates the sclera-iris boundary coordinates (w, h, θp) in the ellipsoidal coordinate system by substituting the sclera-iris boundary coordinates (x, y) in the X-Y orthogonal coordinate system, the center coordinates (x0, y0) of the pupil contour, the minor axis value a and the major axis value b of the pupil contour, and the inclination φ of the pupil contour (ellipsoidal coordinate system) into the equation system of the above formula (9), and solving (back-calculating) the aforementioned equation system. Subsequently, an elliptic orbit passing through the sclera-iris boundary coordinates is acquired by converting coordinates (w, h, θp) of the ellipsoidal coordinate system into coordinates (x, y) of the X-Y orthogonal coordinate system in the above formula (9) equation system, while changing the rotational angle coordinate θp in various ways with the parameters w and h of the sclera-iris boundary coordinates (w, h, θp) in the ellipsoidal coordinate system being fixed.

Next, the reference information acquisition unit 40 sets a detection area of a blood vessel end, on the basis of the elliptic orbit passing through the sclera-iris boundary coordinates acquired as described above. FIG. 14 illustrates an exemplary detection area of a blood vessel end which has been set on the basis of an elliptic orbit Eorbit passing through the sclera-iris boundary coordinates. In the present embodiment, an area extending from the elliptic orbit Eorbit to a position separated away by ten pixels (white band-like area in FIG. 14) is set as a detection area 50 of a blood vessel end. In the present embodiment, the detection area 50 may be set around the entire perimeter of the ellipse representing the boundary between the iris region 102 and the sclera region 103, or may be set in an area of a predetermined angle range (such as 90 degrees, 180 degrees, etc.) along the direction around the ellipse. In other words, the detection area 50 may be provided in a part of the ellipse representing the boundary between the iris region 102 and the sclera region 103, in the present embodiment.

Next, the reference information acquisition unit 40 extracts a blood vessel end in the detection area 50 of the blood vessel end which has been set as described above. FIGS. 15A to 15C are explanatory diagrams of the flow of image processing for extracting a blood vessel end in the detection area 50. FIG. 15A is the original images of a partial area within the detection area 50, FIG. 15B is an image after binarizing the original image, and FIG. 15C is an image after further performing thinning noise removal processing on the binarized image.

In the processing of extracting of a blood vessel end, the reference information acquisition unit 40 first performs smoothing processing on the original image with 19×19 pixel range being the basic unit of processing. Subsequently, the reference information acquisition unit 40 calculates the difference between the original image illustrated in FIG. 15A and the image subjected to the smoothing processing. In the eye image, the pixel values of a blood vessel are lower than the pixel values of the sclera region which is the background. Therefore, the difference value in the blood vessel area tends to be high, the difference value in the sclera region which is the background tends to be low, and the difference value tends to be an approximately constant value in the sclera region, in the image subjected to the difference processing.

Subsequently, the reference information acquisition unit 40, performs the smoothing processing on the image acquired by the aforementioned difference processing with a 3×3 pixel range being the basic unit of processing and removes the salt-and-pepper noise. The reference information acquisition unit 40 then performs binarization, using the threshold, on the image subjected to the smoothing processing. The processing results in a binarized image as illustrated in FIG. 15B, the binarized image making the blood vessel area (black part in FIG. 15B) recognizable.

Subsequently, the reference information acquisition unit 40 performs the noise removal processing on the blood vessel area in the image which has been binarized as described above, using Hilditch's thinning algorithm, similarly to the aforementioned first embodiment. Consequently, an image with a plurality of thin lines (blood vessel part) drawn therein is acquired, as illustrated in FIG. 15C.

Next, the reference information acquisition unit 40 calculates a position closest to the pupil center 101a in respective thin lines acquired in the image illustrated in FIG. 15C, and sets the position as the position of the blood vessel end. The reference information acquisition unit 40 then extracts, from the eye image subjected to the noise removal processing on the basis of Hilditch's thinning algorithm, an image of a 20×20 pixel area with the blood vessel end being the center for every blood vessel end, and acquires an image of the extracted area as a template video image (template image).

Figure 16:
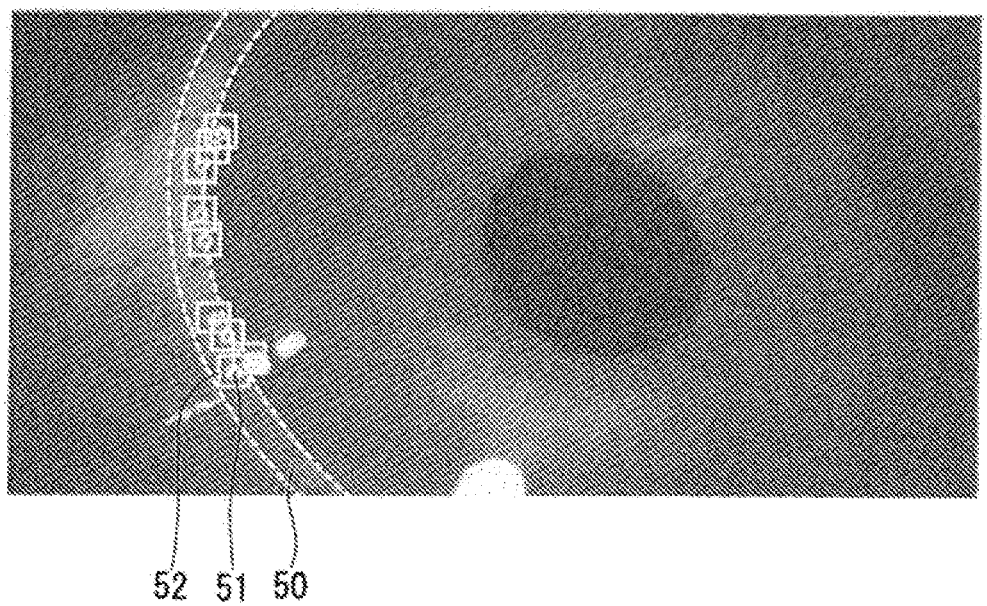
FIG. 16 illustrates the relation between end points of the plurality of conjunctival blood vessels detected in the reference state and areas of template video images of respective conjunctival blood vessels.

FIG. 16 illustrates a plurality of blood vessel ends 51 detected in detection area 50, and areas 52 of a plurality of template video images respectively corresponding thereto. The circle mark in FIG. 16 indicates the blood vessel end 51, and the area surrounded by square white frames is the area 52 of the template video image.

Subsequently, the reference information acquisition unit 40 outputs ellipsoidal coordinates (w, h, θp) of the plurality of blood vessel ends 51 in the detection area 50 acquired in this manner and the plurality of template video images respectively corresponding to the plurality of blood vessel ends 51, together with the difference vector data of the iris shading pattern and the ellipse parameters of the pupil contour (for example, information pertaining to the position of the pupil center 101a, the major axis value, the minor axis value, the rotational angle of the major axis, etc.) in the reference state to the memory device 18 or the auxiliary storage device 16 (see FIG. 1) as the reference information. At the time of acquisition of reference information, various reference information is acquired by the reference information acquisition unit 40 as described above, and the various reference information is stored in the memory device 18 or the auxiliary storage device 16. The ellipsoidal coordinates (w, h, θp) of the blood vessel end 51 are calculated using the above formula (9).

(3) Processing by the Iris Pattern Recognition Processing Unit

The processing by the iris pattern recognition processing unit 42 in the present embodiment is the same as that of the aforementioned first embodiment. Specifically, the iris pattern recognition processing unit 42 calculates the first angle of cycloduction θ1 (denoted as "θ_iris" in the present embodiment), on the basis of the difference vector data of the iris shading pattern recognized in the eye image acquired when actually measuring cycloduction and the difference vector data of the iris shading pattern in the reference state, similarly to the aforementioned first embodiment.

(4) Processing by the Blood Vessel Position Recognition Unit (Template Matching Processing)

In the aforementioned first embodiment, there has been described a method which specifies (selects), from a plurality of blood vessel ends recognized in the eye image acquired when actually measuring cycloduction, an end point closest to the reference end point (Oref) of the blood vessel end which has been acquired using the first angle of cycloduction θ_iris (reference angle of cycloduction), as a blood vessel end for cycloduction measurement (the target end point Otgt of the corresponding blood vessel). However, in the present embodiment, the blood vessel end for cycloduction measurement is specified (selected) in the eye image when actually measuring, by using a different method from the aforementioned first embodiment.

The specification (selection) method of a blood vessel end for cycloduction measurement in the present embodiment is outlined as follows. First, there is performed matching processing (hereinafter, referred to as template matching processing), in the eye image when actually measuring, between an image of a predetermined area (matching area) which has been set on the basis of position information of each blood vessel end acquired at the time of the reference state and a corresponding template video image acquired at the time of the reference state. Subsequently, a blood vessel end with the maximum similarity acquired by the template matching processing is selected as the blood vessel end for cycloduction measurement, and the angle of cycloduction θ is measured on the basis of the selected blood vessel end.

Namely, in the present embodiment, a method of template matching is used as a method of selecting a blood vessel (blood vessel end) which is the target of measuring the angle of cycloduction θ. The aforementioned template matching processing is performed in the blood vessel position recognition unit 44. Meanwhile, since the processing performed by the blood vessel position recognition unit 44 other than the template matching processing are the same as the processing in the aforementioned first embodiment, description of the processing is omitted here and the template matching processing will be described.

Furthermore, although it is also possible to perform the template matching processing on the entire range of the eye image (the matching area being set all over the eye image), the processing cost increases in such case. Therefore, in the present embodiment, the matching area is narrowed down using the first angle of cycloduction θ_iris calculated by the conventional cycloduction measurement method based on the shading pattern of the iris image (on the basis of the above formula (1)).

Figure 17:
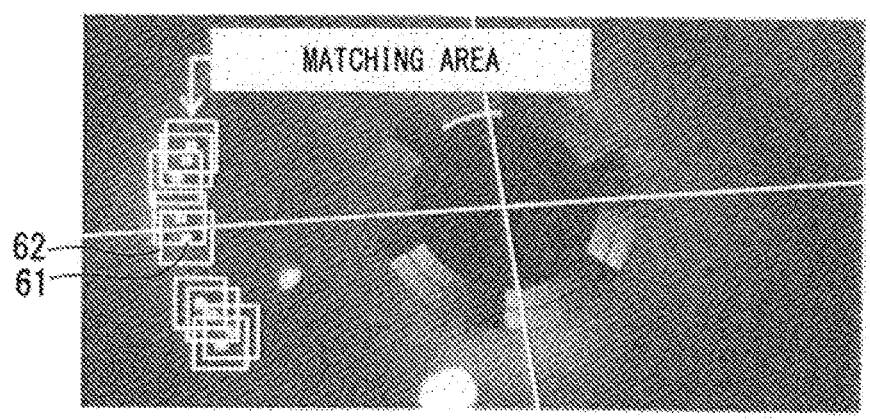
FIG. 17 illustrates the relation between areas (matching areas) which are set when actually measuring cycloduction to be subjected to a template matching processing, and the reference end points when setting the areas.

FIG. 17 is a diagram illustrating an example of matching areas 62 to which the template matching processing is applied, and reference end points 61 for determining the matching area 62, in the present embodiment. Meanwhile, the white square dot in FIG. 17 indicates reference end point 61, and the area surrounded by square white frame is the matching area 62.

Here, a setting method of a plurality of reference end points 61 and a plurality of matching areas 62 respectively corresponding thereto as illustrated in FIG. 17 will be described.

First, the blood vessel position recognition unit 44 calculates the reference end points 61 of the matching areas 62 by using the first angle of cycloduction θ_iris calculated by the conventional cycloduction measurement method based on the shading pattern of the iris image.

Figure 18:
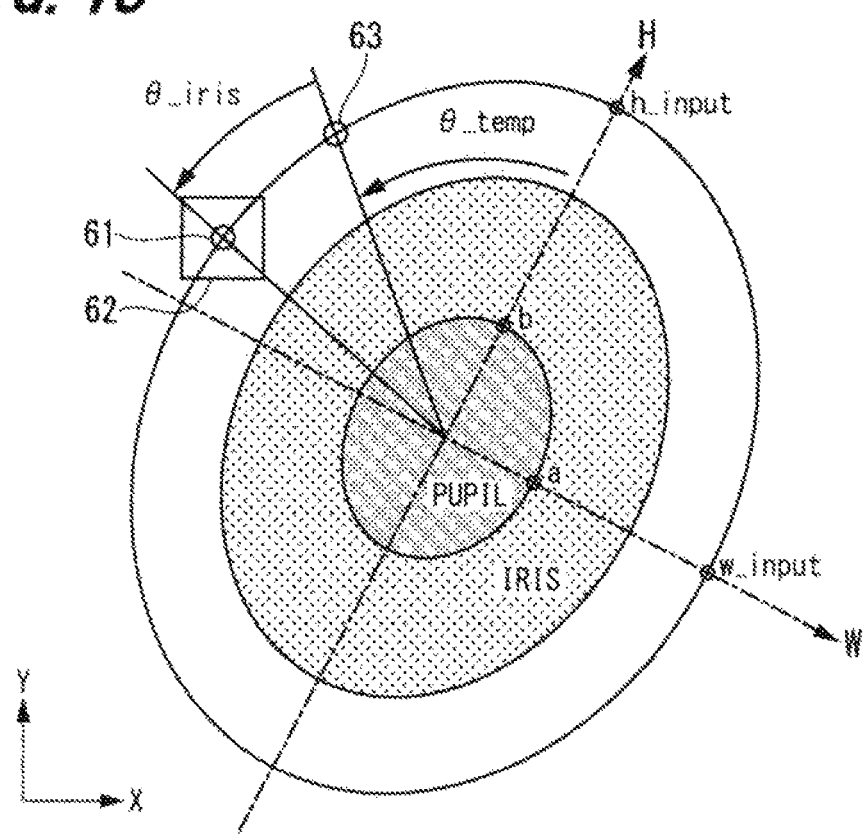
FIG. 18 is an explanatory diagram of a setting method of an area (matching area) to be subjected to template matching processing.

FIG. 18 illustrates the outline of a calculation method of the reference end points 61 of the matching areas 62. Meanwhile, in FIG. 18, for simplification of the explanation, only a matching area 62 and the reference end point 61 for a single blood vessel end 63 are illustrated.

In the present embodiment, a rotational angle coordinate (initial position) in the ellipsoidal coordinate system of each blood vessel end 63 in the reference state is denoted as θ_temp, as illustrated in FIG. 18, on the ellipse passing through the position of each blood vessel end 63 acquired as the reference information. In addition, the blood vessel position recognition unit 44 then sets a position (θ_input) resulting from further rotating counter-clockwise relative to the major axis of the ellipse by the first angle of cycloduction θ_iris from the initial position θ_temp, as the reference end point 61 for setting the matching areas 62. Namely, the blood vessel position recognition unit 44 calculates the rotational angle coordinate θ_input of the reference end point 61 by using the following formula (10). Meanwhile, the shape of the ellipse passing through the position of each blood vessel end 63 (each reference end point 61) is homothetic with the elliptical shape of the pupil contour.

[Expression 6]

$$\theta\_input = \theta\_temp + \theta\_iris \quad (10)$$

The coordinates (x, y) of the reference end point 61 in the X-Y orthogonal coordinate system of the camera video image (eye image) can be obtained by substituting the rotational angle coordinate θ_input of the reference end point 61 when actually measuring cycloduction (rotation component when moving the line of sight), the center coordinates (x0_input, y0_input) of the pupil ellipse when actually measuring, the inclination φ_input of the pupil ellipse when actually measuring, and the coordinate h_input in the major axis direction (major axis value) and the coordinate w_input in the minor axis direction (minor axis value) of the ellipse passing through the reference end point 61 into the above formula (9). The ellipse parameters of the pupil when actually measuring cycloduction are preliminarily acquired before calculating the first angle of cycloduction θ_iris by the iris pattern recognition processing unit 42, in the same manner as the aforementioned first embodiment.

Subsequently, the blood vessel position recognition unit 44 sets a predetermined range of area having the reference end point 61 being the center, as the matching area 62. Accordingly, as illustrated in FIG. 17, a plurality of reference end points 61 and a plurality of matching areas 62 respectively corresponding thereto are set. Meanwhile, in the example illustrated in FIGS. 17 and 18, a 40×40 pixel range with the reference end point 61 being a center is assumed to be the matching area 62. Additionally, in the example, the size of the template video image of each blood vessel end acquired at the time of acquisition of reference information is set to be 20×20 pixels.

Next, the blood vessel position recognition unit 44 performs matching processing between an image of each matching areas 62 (referred to as input video image) and a template video image of a corresponding blood vessel end. Meanwhile, in the present embodiment, the blood vessel position recognition unit 44 performs a preprocessing of the template matching processing so that the maximum pixel value is 255 and the minimum pixel value is 0 respectively on the template video image and the input video image to thereby raise the contrast of the blood vessel end. In addition, the blood vessel position recognition unit 44 then performs template matching using the video image subjected to the contrast enhancement processing. Specifically, the blood vessel position recognition unit 44 calculates the similarity between the input image and the template video image while moving (sliding) the corresponding template video image one pixel by one pixel in each matching area 62.

Meanwhile, in the following description, the center position of the template video image to be shifted (position of the blood vessel end) in each matching area 62 is referred to as the pixel position. Additionally, in the present embodiment, a X-Y orthogonal coordinate system with an origin different from that of the X-Y orthogonal coordinate system of the eye image is separately provided in each matching area 62. The pixel position (position of the blood vessel end) of the template video image in the X-Y orthogonal coordinate system set in each matching area 62 is expressed by the coordinates (xt, yt). Since the size of each matching area 62 is set to be 40×40 pixels and the size of each template video image is set to be 20×20 pixels in the example, the variable range of the parameter xt of the coordinates (xt, yt) indicating the pixel position is equal to or larger than 0 and less than 20, and the variable range of yt is equal to or larger than 0 and less than 20.

In addition, in the present embodiment, ZNCC (Zero-mean Normalized Cross-Correlation) is used as the method of calculating similarity by the template matching processing. When the similarity using ZNCC is set to be R_zncc, the similarity R_zncc (xt, yt) in each pixel position is obtained by the following formulae (11) to (13).

[Expression 7]

$$R\_zncc(x_t, y_t) = \frac{\sum_{i=0}^{M-1}\sum_{j=0}^{N-1}((I(i,j) - \bar{I})(T(i+x_t, j+y_t) - \bar{T}))}{\sqrt{\sum_{i=0}^{M-1}\sum_{j=0}^{N-1}(I(i,j) - \bar{I})^2}\sqrt{\sum_{i=0}^{M-1}\sum_{j=0}^{N-1}(T(i,j) - \bar{T})^2}} \quad (11)$$

$$\bar{I} = \frac{1}{MN}\sum_{i=0}^{M-1}\sum_{j=0}^{N-1}I(i,j) \quad (12)$$

$$\bar{T} = \frac{1}{MN}\sum_{i=0}^{M-1}\sum_{j=0}^{N-1}T(i,j) \quad (13)$$

T(i, j) in the above formulae (11) to (13) is the pixel value of the pixel of the coordinates (i, j) in the template video image, and I(i, j) is the pixel value of the input video image in the coordinates (i, j), and M and N are the width (number of pixels) in the vertical direction and the width in the horizontal direction (number of pixels) of the template video image, respectively. In the example, M=20 and N=20 are set because the size of each template video image is set to be 20×20 pixels.

Subsequently, the blood vessel position recognition unit 44 calculates the similarity R_zncc (xt, yt) in each pixel position while sliding each template video image (while changing the pixel position) in the corresponding matching area 62. The blood vessel position recognition unit 44 performs this processing on all of the set matching areas 62. Namely, in the present embodiment, the template matching processing is performed on all of the blood vessel ends detected in the detection area 50 in the eye image in the reference state and the similarity R_zncc is calculated.

Meanwhile, in the above formula (11), the similarity is normalized by dividing the mutual correlative function (numerator in formula (11)) between the input image and the template video images by the variance of the pixel values in the input video image and the variance of the pixel values in the template video image. In such case, the use of a video image (input image and/or template video image) of the blood vessel end including noise such as an eyelash or illumination results in a low similarity R_zncc. On the other hand, the use of a video image of the blood vessel end not including noise results in a relatively higher similarity R_zncc than the similarity R_zncc in the case of using a video image of the blood vessel end including noise. Therefore, measurement of cycloduction with little effect of noise can be performed by selecting a blood vessel end having the highest similarity R_zncc from among the similarities calculated for all of the blood vessel ends, and by calculating the angle of cycloduction θ using the blood vessel end.

Therefore, in the present embodiment, the blood vessel position recognition unit 44 selects a blood vessel end having the highest similarity R_zncc (center of the template video image) as the blood vessel end for cycloduction measurement, on the basis of the result of the template matching processing performed on all of the matching areas 62, and specifies the pixel position (xt, yt) of the blood vessel end for cycloduction measurement. Accordingly, it is possible to specify the position of the blood vessel end with the least influence of the aforementioned noise.

Subsequently, the blood vessel position recognition unit 44 converts coordinates (xt, yt) of the pixel position of the blood vessel end for cycloduction measurement (coordinates in the X-Y orthogonal coordinate system separately set in the matching area 62) into coordinates (x, y) in the X-Y orthogonal coordinate system of the camera video image (eye image). Accordingly, position information of the blood vessel end for cycloduction measurement in the X-Y orthogonal coordinate system of the camera video image (eye image) is acquired. Subsequently, the blood vessel position recognition unit 44 substitutes the position coordinates (x, y) of the blood vessel end for angle of cycloduction measurement into the above formula (9), and calculates the rotational angle coordinate θ_out (a first information pertaining to the position of the predetermined blood vessel) in the ellipsoidal coordinate system of the blood vessel end for angle of cycloduction measurement by back-calculating the equation system of the above formula (9).

In the present embodiment, the blood vessel position recognition unit 44 automatically selects a blood vessel end being least affected by noise when actually measuring from a plurality of blood vessel ends detected in the reference state, as described above, and acquires the position information thereof.

(5) Processing by the Angle Calculation Unit

In the present embodiment, the angle of cycloduction θ indicates the amount of change of the rotational angle coordinate when the rotational angle coordinate θp of the blood vessel end having the highest similarity R_zncc selected by the blood vessel position recognition unit 44 (blood vessel end for cycloduction measurement) changes from the initial position θ_temp to the rotational angle coordinate θ_out when actually measuring. Therefore, the angle calculation unit 46 subtracts the initial position θ_temp (a second information pertaining to the position of the predetermined blood vessel) from the rotational angle coordinate θ_out when actually measuring (a first information pertaining to the position of the predetermined blood vessel) in the blood vessel end for angle of cycloduction measurement to calculate the angle of cycloduction θ (=θ_out−θ_temp).

[Flow Chart of the Cycloduction Measurement Processing]

Figure 19:
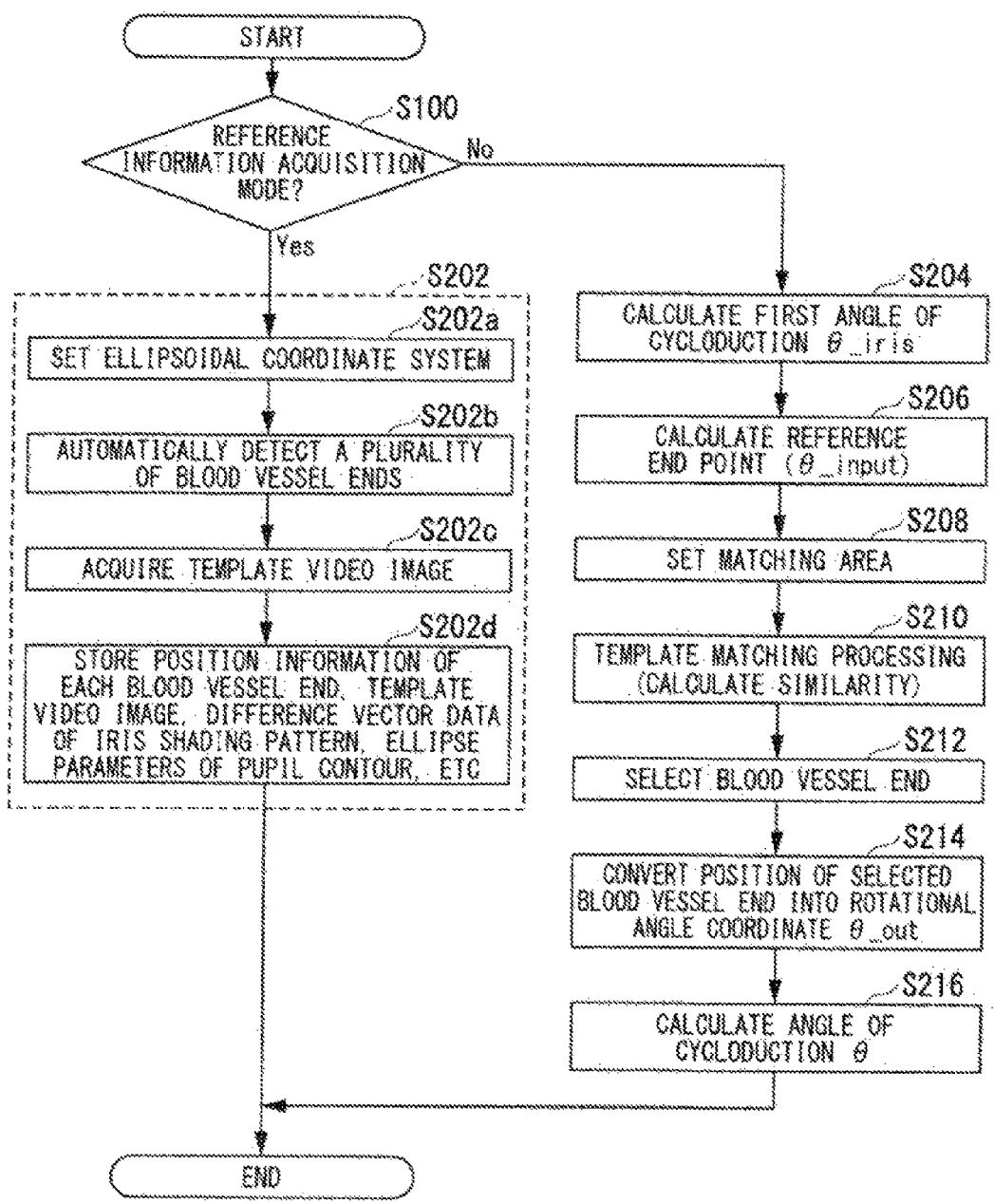
FIG. 19 is a flow chart illustrating a processing procedure of the cycloduction measurement method according to the second embodiment.

Next, a specific processing procedure when cycloduction measurement is performed by the cycloduction measurement device 1 of the present embodiment will be described, referring to FIG. 19. FIG. 19 is a flow chart illustrating a processing procedure of the cycloduction measurement method performed by the cycloduction measurement device 1 of the present embodiment. Meanwhile, in the flow chart of the present embodiment illustrated in FIG. 19, the same reference numerals are attached to processing (steps) similar to those in the flow chart of the aforementioned first embodiment illustrated in FIG. 11.

First, the cycloduction measurement device 1 determines whether or not the current measurement mode is the reference information acquisition mode, in the same manner as the aforementioned first embodiment (S100).

When the current measurement mode is the reference information acquisition mode at S100, the result of determination at S100 is Yes. In such case, the cycloduction measurement device 1 analyzes the subject's eye image acquired in a state without any pupil change or cycloduction (reference state) and acquires various pieces of reference information (S202). Although not illustrated in FIG. 19, in the present embodiment, the difference vector data of the iris shading pattern in the reference state is acquired as a piece of reference information at the time of acquisition of reference information as described above, in the same manner as the aforementioned first embodiment.

Here, the processing of S202 will be described more specifically. At S202, the cycloduction measurement device 1, first, binarizes the eye image in the reference state, and performs ellipse approximation (ellipse fitting processing) on the pupil region in the binarized eye image. Consequently, ellipse parameters (for example, information pertaining to the center point of the pupil contour, the major axis value, the minor axis value, the rotational angle of the major axis, etc.) of the pupil contour in the reference state is acquired. In addition, the cycloduction measurement device 1 sets the ellipsoidal coordinate system along the pupil contour (basic ellipsoidal coordinate system) through the use of various ellipse parameters of the pupil contour calculated by ellipse approximation (S202*a*).

Next, the cycloduction measurement device 1 calculates the sclera-iris boundary coordinates on the basis of, for example, the method described in FIGS. 12 and 13. Subsequently, the cycloduction measurement device 1 sets the detection area 50 of the blood vessel end in the vicinity of the periphery of the iris region, on the basis of the ellipse passing through the sclera-iris boundary coordinates (periphery of the iris region), as described in FIG. 14, for example. In addition, on the basis of, for example, the method described in FIGS. 15A to 15C, the cycloduction measurement device 1 then automatically detects a plurality of blood vessel ends 51 in the set detection area 50 (S202b). Meanwhile, in the processing of S202b, position information of each blood vessel end 51 is acquired.

Subsequently, the cycloduction measurement device 1 acquires an image of the area 52 of a predetermined size with each blood vessel end 51 detected at S202b being the center as the template video image, as illustrated in, for example, FIG. 16 (S202c).

After that, the cycloduction measurement device 1 stores information acquired in the aforementioned various pieces of processing, such as the position information of each blood vessel end 51, the template video image corresponding to each blood vessel end 51, the difference vector data of the iris shading pattern, the ellipse parameters (for example, information pertaining to the center point of the pupil contour, the major axis value, the minor axis value, the rotational angle of the major axis, and the like) of the pupil contour in, for example, the memory device 18 or the auxiliary storage device 16, as the reference information (S202d). In addition, after having performed the processing of S202d, the cycloduction measurement device 1 terminates the processing of S202 and also terminates the cycloduction measurement processing.

Here, returning to the processing of S100 again, various pieces of processing performed when the result of determination at S100 is No will be described.

When the current measurement mode is not the reference information acquisition mode at S100, that is, when the current measurement mode is the actual measurement mode of cycloduction, the result of determination at S100 is No. In such case, the cycloduction measurement device 1 analyzes the eye image when actually measuring acquired from the same subject as when the reference information is acquired at S202, and calculates the first angle of cycloduction θ_iris on the basis of the iris shading pattern recognized in the eye image when actually measuring (S204). Meanwhile, in the processing of S204, the cycloduction measurement device 1 calculates the first angle of cycloduction θ_iris according to the aforementioned processing operation of the iris pattern recognition processing unit 42.

Next, the cycloduction measurement device 1 calculates the reference end point 61 for setting the matching area 62 of each blood vessel end 51, through the use of the first angle of cycloduction θ_iris calculated at S204 and the position information of each blood vessel end 51 (initial position θ_temp) acquired as the reference information, as described in FIGS. 17 and 18 (S208). Specifically, the cycloduction measurement device 1 calculates the rotational angle coordinate θ_input in the ellipsoidal coordinate system of the reference end point 61 of each matching area 62 according to the above formula (10).

Subsequently, the cycloduction measurement device 1 sets the matching area 62 of a predetermined range (40×40 pixels in the example illustrated in FIGS. 17 and 18) with the reference end point 61 as a center (S208).

After that, the cycloduction measurement device 1 performs template matching processing between an image in each matching area 62 and a corresponding template video image (S210). In the processing of S210, the cycloduction measurement device 1 calculates the similarity R_zncc in all of the matching areas 62 (all of the extracted blood vessel ends 51) by using the above formulae (11) to (13).

Next, the cycloduction measurement device 1 selects (specifies) the blood vessel end 51 having the highest similarity, from a plurality of similarities R_zncc calculated at S210, as a blood vessel end for cycloduction measurement (S212). In the present embodiment, the position coordinates (x, y) in the X-Y orthogonal coordinate system of the blood vessel end 51 for the cycloduction measurement are acquired by this processing.

Subsequently, the cycloduction measurement device 1 converts the position coordinates (x, y) in the X-Y orthogonal coordinate system of the blood vessel end 51 for cycloduction measurement selected at S212 into the rotational angle coordinate θ_out in the ellipsoidal coordinate system (S214). Meanwhile, the coordinate conversion processing of the blood vessel end 51 is performed using the above formula (9). The rotational angle coordinate θ_out of the blood vessel end 51 calculated at S214 is the angle position of the blood vessel end 51 after cycloduction that best matches the blood vessel end of the initial image.

In addition, the cycloduction measurement device 1 then calculates the final angle of cycloduction θ through the use of the rotational angle coordinate (initial position θ_temp) in the reference state of the blood vessel end 51 for cycloduction measurement selected at S212, and the rotational angle coordinate θ_out of the blood vessel end 51 for cycloduction measurement calculated at S214 when actually measuring cycloduction (S216).

In the present embodiment, cycloduction is measured as described above. Meanwhile, in the present embodiment, the aforementioned cycloduction measurement processing may be implemented by installing a corresponding cycloduction measurement program in the cycloduction measurement device 1, and by executing the cycloduction measurement program by the CPU 10.

In the aforementioned cycloduction measurement technique of the present embodiment, the angle of cycloduction θ is calculated on the basis of the position of the blood vessel end (end point of the conjunctival blood vessel) having a high contrast to the surrounding and being not much affected by pupil contraction, in the same manner as the aforementioned first embodiment. Additionally, in the present embodiment, the angle of cycloduction θ is calculated on the basis of the position of the blood vessel end existing in the vicinity of the periphery of the iris region that is hardly affected by eyelid movement or the like, in the same manner as the aforementioned first embodiment. Therefore, the present embodiment can also perform cycloduction measurement with higher precision, in the same manner as the aforementioned first embodiment.

Additionally, in the present embodiment, the range of the matching area is narrowed down using the first angle of cycloduction θ_iris calculated by cycloduction measurement method which uses the iris shading pattern, as described above. Therefore, the present embodiment can also perform high-speed and low-cost cycloduction measurement, and measurement of the angle of cycloduction with high precision and a high resolution is possible even when the pupil diameter changes, in the same manner as the aforementioned first embodiment.

Furthermore, in the present embodiment, the blood vessel end being least affected by noise can be automatically detected as a blood vessel end for cycloduction measurement, from among a plurality of blood vessel ends (conjunctival blood vessel ends). Therefore, the present embodiment allows cycloduction to be measured with still higher precision and reliability.

[Evaluation Experiment]

Here, various effects acquired by the cycloduction measurement technique of the aforementioned present embodiment will be specifically described, on the basis of the result of an evaluation experiment actually performed. In the evaluation experiment, the angle of cycloduction θ was calculated in a state where variation of the pupil diameter and cycloduction motion were occurring simultaneously in three subjects, and the average error and standard deviation thereof were measured.

Specifically, first, the subject was caused to wait in the darkroom in order to cause variation of the pupil, and the pupil was enlarged by dark adaptation for about five to six minutes. Video image capturing was started from the time of the pupillary enlargement (a state where the subject was dark-adapted), and in the course of the video image capturing, white LED illumination was irradiated to the subject's pupil to cause pupil contraction. Additionally, in the evaluation experiment, the subject's head was inclined horizontally in order to cause cycloduction motion simultaneously with the video image acquisition processing to thereby induce cycloduction motion due to vestibulo-ocular reflex.

Next, the average error between the true value of the angle of cycloduction θ estimated by visual observation and the measurement value of the angle of cycloduction θ calculated by the cycloduction measuring system illustrated in FIG. 1 and standard deviation thereof were obtained for the 200 video images acquired. Meanwhile, the image resolution of the eye image used in the evaluation experiment was 740× 320 pixels, and the number of blood vessel ends 51 detected in the detection area 50 in the vicinity of the periphery of the iris region was 10. In addition, the resolution of the angle of cycloduction θ, which depends on the length from the pupil center position to the conjunctival blood vessel end, was about 0.25 degrees. The result of the evaluation experiment is illustrated in FIGS. 20A and 20B.

Figures 20A, 20B:
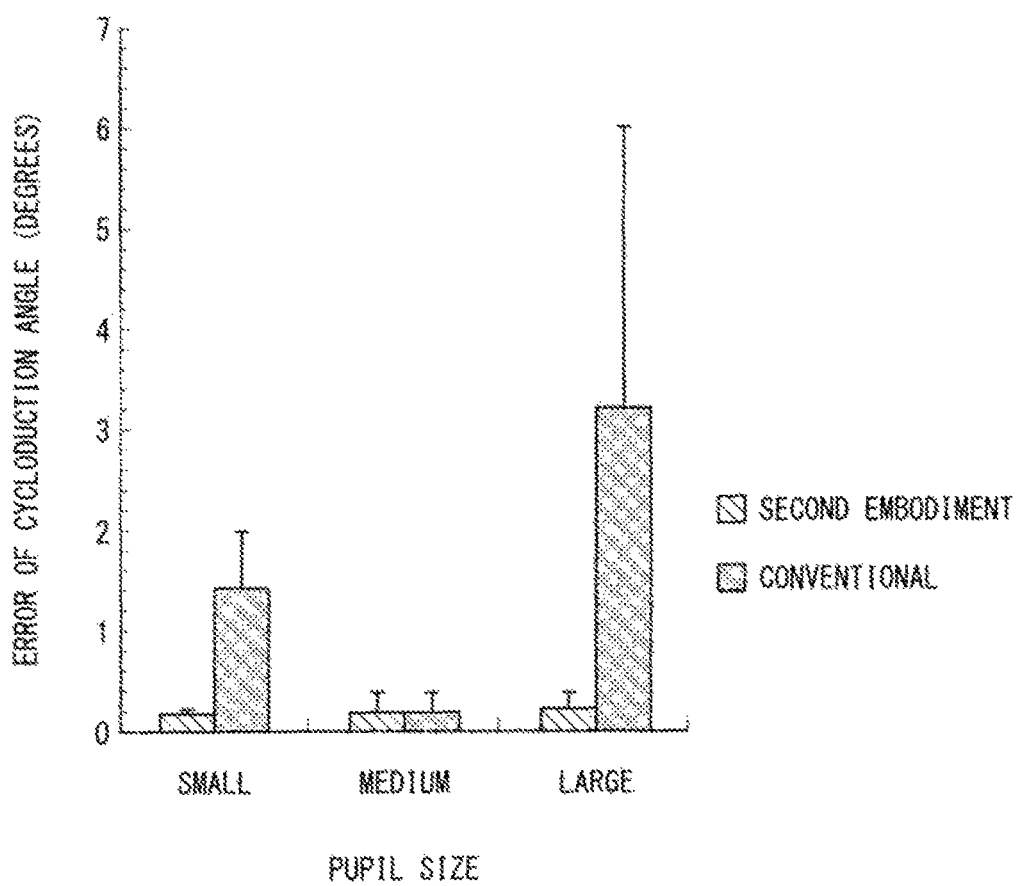
FIGS. 20A and 20B illustrate a result of an evaluation experiment performed using the cycloduction measurement method of the second embodiment.

FIG. 20A illustrates the values of the average error (error of cycloduction angle in FIG. 20A) of the angle of cycloduction θ and standard deviation thereof measured for each pupil size while varying the pupil size in three levels: small, medium and large, in accordance with the length of the major axis of the pupil. As is obvious from the result, in the present embodiment, it is found that the cycloduction can be measured with precision such that the average error of the angle of cycloduction θ is equal to or less than 0.24 degrees even when the pupil diameter changes and an average error close to the resolution is acquired.

In addition, FIG. 20B compares the average error of the angle of cycloduction θ acquired by the cycloduction measurement method according to the present embodiment with the average error of the angle of cycloduction θ acquired by the conventional cycloduction measurement method on the basis of the iris shading pattern. Meanwhile, the vertical axis of the bar graph illustrated in FIG. 20B indicates the average error of the angle of cycloduction θ (error of cycloduction angle in FIG. 20B), and the horizontal axis indicates the pupil size.

As is obvious from the evaluation result of FIG. 20B, when the pupil diameter (pupil size) changes, the error of the angle of cycloduction also varies significantly in the conventional cycloduction measurement method. Particularly, it is found that the larger the pupil diameter is, the larger the error of the angle of cycloduction becomes in the conventional cycloduction measurement method.

On the other hand, in the cycloduction measurement method according to the present embodiment, the change of the error of the angle of cycloduction is small and the error of the angle of cycloduction is equal to or less than 0.24 degrees even if the pupil diameter (pupil size) changes, as is obvious from FIG. 20B. Namely, in the present embodiment, it is found that the cycloduction can be measured with high precision and also without being affected by the change of the pupil diameter.

It is also found from the aforementioned evaluation result that, according to the cycloduction measurement technique of the present embodiment, the angle of cycloduction θ can be measured with a resolution of about several tenths of a degree and cycloduction can be measured with higher precision than the conventional method (method which uses the iris shading pattern).

<3. Various Modifications and Applications>

The cycloduction measurement device, the cycloduction measurement method, and the cycloduction measurement program according to the present invention are not limited to the examples described in the aforementioned various embodiments. Various types of other modifications are also included in the present invention as long as they do not deviate from the gist of the present invention described in the appended claims. For example, the following various modifications and applications are also included in the present invention.

[Exemplary Modification 1]

In the aforementioned second embodiment, although there has been described an example (see FIG. 18) in which the first angle of cycloduction θ_iris is calculated by the conventional cycloduction measurement method on the basis of the shading pattern of the iris image and the range of the matching area for specifying a blood vessel end for cycloduction measurement is narrowed down using the first angle of cycloduction θ_iris, the present invention is not limited thereto. For example, a matching area including the blood vessel end may be directly set from the position information of the blood vessel end detected at the time of acquisition of reference information without calculating the first angle of cycloduction θ_iris. In such case, it is necessary to set a matching area having a wider size than the matching areas 62 set in the aforementioned second embodiment. An example of such a matching area setting method is illustrated in FIG. 21.

Figure 21:
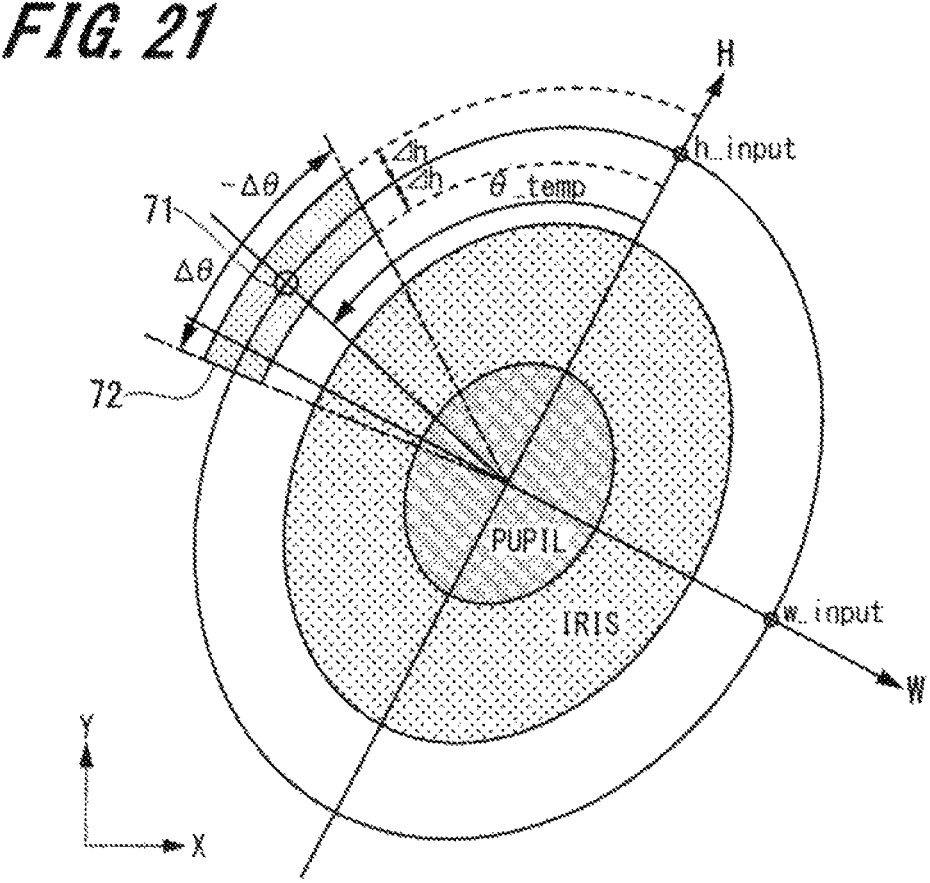
FIG. 21 is an explanatory diagram of the setting method of the area (matching area) to be subjected to the template matching processing in an exemplary modification 1.

FIG. 21 illustrates the outline of the setting method of a matching area 72 in an exemplary modification 1. Meanwhile, in FIG. 21, only a single blood vessel end 71 and a matching area 72 set therefor are illustrated for simplification of the explanation.

In the example, an area extending a predetermined width (2Δh) across an angle range of ±Δθ relative to the initial position θ_temp of each blood vessel end 71 (target end point) in the ellipse passing through each blood vessel end 71 detected in the vicinity of the periphery of the iris region at the time of acquisition of reference information is set as the matching area 72. Meanwhile, the angle width Δθ defining the range of the rotational direction on the ellipse of the matching area 72 and the width Δh defining the range of the radial direction of an ellipse can be set as appropriate, considering, for example, the maximum amount of travel of the blood vessel end 71 assumed at the time of occurrence of ocular motion including cycloduction motion. For example, the angle width Δθ may be 20 degrees and the width Δh may be about 20 pixels.

Meanwhile, the setting range of the matching area 72 in the example is not limited to the example illustrated in FIG. 21. For example, an area extending a predetermined width (2Δh) over the whole circumference of the ellipse passing through each blood vessel end 71 detected in the vicinity of the periphery of the iris region at the time of acquisition of reference information may be set as the matching area.

In the method of the example, the angle of cycloduction θ is also calculated on the basis of the position of the blood vessel end (end point of the conjunctival blood vessel) having a high contrast to the surrounding and being not much affected by pupil contraction, in the same manner as the second embodiment. Therefore, also in the cycloduction measurement technique of the example, cycloduction can be measured with higher precision, in the same manner as the second embodiment.

Meanwhile, in the example, a matching area including the blood vessel end is directly set from the position information of the blood vessel end detected at the time of acquisition of reference information, and thus also the matching area becomes wide as described above. Therefore, the second embodiment is more advantageous from the viewpoint of the high-speed performance of cycloduction measurement.

[Exemplary Modification 2]

In the aforementioned first embodiment, although a blood vessel having a target end point which is closest to the reference end point (Oref) of the blood vessel end acquired using the first angle of cycloduction θ1 is selected as the corresponding blood vessel when specifying, from a plurality of blood vessels recognized in the eye image acquired when actually measuring cycloduction, a corresponding blood vessel (blood vessel corresponding to the predetermined blood vessel selected in the eye image in the reference state), the present invention is not limited thereto. The corresponding blood vessel may be specified in the eye image acquired when actually measuring cycloduction, through the application of the template matching processing described in the second embodiment to the aforementioned first embodiment.

In such case, at the time of acquisition of the reference state, a template video image of a predetermined size is acquired, with the target end point Otgt0 of the predetermined blood vessel (blood vessel for the cycloduction measurement) selected in the eye image on the reference state being the center. In addition, a matching area of a predetermined size is set when actually measuring cycloduction, with the reference end point (Oref) of each blood vessel end acquired using the first angle of cycloduction θ1 being the center point. Thereafter, matching processing between the matching area and the template video image is performed, and a corresponding blood vessel is specified from a plurality of blood vessels recognized in the eye image acquired when actually measuring, in the same manner as the aforementioned second embodiment.

Furthermore, the corresponding blood vessel may be specified from a plurality of blood vessels recognized in the eye image acquired when actually measuring cycloduction, through the application of the template matching processing described in the aforementioned modification 1 to the aforementioned first embodiment.

Also in such case, at the time of acquisition of the reference state, a template video image of a predetermined size is acquired, with the target end point Otgt0 of the predetermined blood vessel (blood vessel for cycloduction measurement) selected in the eye image in the reference state being the center. In addition, when actually measuring cycloduction, a matching area of a predetermined size is set, with the target end point Otgt0 of the predetermined blood vessel selected in the reference state as a center point. The matching area in such case is provided along the ellipse passing through the target end point Otgt0 of the predetermined blood vessel, as described in FIG. 21. Thereafter, matching processing between the matching area and the template video image is performed, in the same manner as the aforementioned modification 1, and a corresponding blood vessel is specified in the eye image acquired when actually measuring.

[Other Various Modifications]

Although an example of setting an area for detecting the blood vessel end (end point at the pupil side of the conjunctival blood vessel) outside the iris region (including the periphery of the iris region) has been described in the aforementioned various embodiments and modifications thereof, the present invention is not limited thereto. The detection area of the blood vessel end may be set in any region in the vicinity of the periphery of the iris region. For example, the detection area may be set so that a part of the detection area includes an area inside (the pupil side) of the periphery of the iris region.

In addition, although an example of calculating the angle of cycloduction θ on the basis of the position of the end point of the conjunctival blood vessel has been described in the aforementioned various embodiments and modifications thereof, the present invention is not limited thereto. For example, the angle of cycloduction θ may be calculated by making a comparison between the extending direction of the predetermined blood vessel in the eye image in the reference state and the extending direction of a blood vessel corresponding to the predetermined blood vessel in the eye image when actually measuring.

APPLICATION

The aforementioned technique of the present invention can be applied not only to the measurement technique of cycloduction but also to the measurement technique of overall ocular motion such as visual line detection, and the same effect can be obtained.

REFERENCE SIGNS LIST

1 . . . cycloduction measurement device, 10 . . . CPU, 16 . . . auxiliary storage device, 18 . . . memory device, 26 . . . image input interface, 30 . . . camera, 32 . . . infrared LED, 34 . . . blue LED, 40 . . . reference information acquisition unit, 42 . . . iris pattern recognition processing unit, 44 . . . blood vessel position recognition unit, 46 . . . angle calculation unit, 50 . . . detection area, 51,63 . . . position of blood vessel end in reference state, 52 . . . template video image area, 61 . . . reference end point, 62 . . . matching area, 100 . . . eye image, 101 . . . pupil region, 101a . . . center of pupil contour, 102 . . . iris region, 103 . . . sclera region, 104 . . . blood vessel, a 04a . . . blood vessel end

The invention claimed is:

1. A cycloduction measurement device, comprising:
a reference information acquisition unit configured to acquire ellipse parameters of a pupil contour by performing ellipse fitting processing on the pupil contour in an eye image of a subject being in a reference state;
a blood vessel position recognition unit configured to recognize a position of a blood vessel in a sclera region in an eye image of the subject and acquire information pertaining to the position of the blood vessel; and
a first angle calculation unit configured to calculate an angle of cycloduction, on the basis of a first information pertaining to a position of a predetermined blood vessel acquired by the blood vessel position recognition unit when actually measuring cycloduction, a second information pertaining to the position of the predetermined blood vessel in the reference state, and the ellipse parameters of the pupil contour acquired by the reference information acquisition unit.

2. The cycloduction measurement device according to claim 1,
wherein the blood vessel position recognition unit acquires position information of an end point of the blood vessel, as information pertaining to the position of the blood vessel.

3. The cycloduction measurement device according to claim 2,
wherein the blood vessel position recognition unit recognizes a periphery of an iris region in the eye image, and acquires position information of an end point at the peripheral side of the iris region of the blood vessel as information pertaining to the position of the blood vessel.

4. The cycloduction measurement device according to claim 2, comprising
a second angle calculation unit configured to calculate a reference angle of cycloduction, on the basis of an iris shading pattern in the eye image, wherein
the blood vessel position recognition unit determines an assumed end point position of the predetermined blood vessel on the basis of the reference angle of cycloduction calculated by the second angle calculation unit and the second information pertaining to the position of the predetermined blood vessel in the reference state, and acquires position information of an end point of a blood vessel existing in a position which is closest to the assumed end point position among end points of one or more blood vessels recognized from an eye image when actually measuring cycloduction, as the first information pertaining to the position of the predetermined blood vessel.

5. The cycloduction measurement device according to claim 3, comprising
a second angle calculation unit configured to calculate a reference angle of cycloduction, on the basis of an iris shading pattern in the eye image, wherein
the blood vessel position recognition unit determines an assumed end point position of the predetermined blood vessel on the basis of the reference angle of cycloduction calculated by the second angle calculation unit and the second information pertaining to the position of the predetermined blood vessel in the reference state, and acquires position information of an end point of a blood vessel existing in a position which is closest to the assumed end point position among end points of one or more blood vessels recognized from an eye image when actually measuring cycloduction, as the first information pertaining to the position of the predetermined blood vessel.

6. The cycloduction measurement device according to claim 3,
wherein the blood vessel position recognition unit detects end points of one or more blood vessels existing in a detection area which is provided along the periphery of the iris region and which includes the sclera region, sets, for the end point of each detected blood vessel, a matching area including the end point, calculates similarity between an image of the matching area and a template image of a predetermined size in the reference state of a blood vessel corresponding thereto, and acquires position information of an end point at which the similarity is maximal, as the first information pertaining to the position of the predetermined blood vessel.

7. The cycloduction measurement device according to claim 6,
wherein the blood vessel position recognition unit sets, for the end point of each detected blood vessel, a predetermined area having the end point being a center, as the matching area.

8. The cycloduction measurement device according to claim 1,
wherein the blood vessel position recognition unit recognizes a periphery of an iris region in the eye image, and acquires position information of an end point at the peripheral side of the iris region of the blood vessel as information pertaining to the position of the blood vessel.

9. The cycloduction measurement device according to claim 8,
wherein the blood vessel position recognition unit detects end points of one or more blood vessels existing in a detection area which is provided along the periphery of the iris region and which includes the sclera region, sets, for the end point of each detected blood vessel, a matching area including the end point, calculates similarity between an image of the matching area and a template image of a predetermined size in the reference state of a blood vessel corresponding thereto, and acquires position information of an end point at which the similarity is maximal, as the first information pertaining to the position of the predetermined blood vessel.

10. The cycloduction measurement device according to claim 9,
wherein the blood vessel position recognition unit sets, for the end point of each detected blood vessel, a predetermined area having the end point being a center, as the matching area.

11. The cycloduction measurement device according to claim 1, comprising
a second angle calculation unit configured to calculate a reference angle of cycloduction, on the basis of an iris shading pattern in the eye image, wherein
the blood vessel position recognition unit determines an assumed end point position of the predetermined blood vessel on the basis of the reference angle of cycloduction calculated by the second angle calculation unit and the second information pertaining to the position of the predetermined blood vessel in the reference state, and acquires position information of an end point of a blood vessel existing in a position which is closest to the assumed end point position among end points of one or more blood vessels recognized from an eye image when actually measuring cycloduction, as the first information pertaining to the position of the predetermined blood vessel.

12. The cycloduction measurement device according to claim 8, comprising
a second angle calculation unit configured to calculate a reference angle of cycloduction, on the basis of an iris shading pattern in the eye image, wherein
the blood vessel position recognition unit determines an assumed end point position of the predetermined blood vessel on the basis of the reference angle of cycloduction calculated by the second angle calculation unit and the second information pertaining to the position of the predetermined blood vessel in the reference state, and acquires position information of an end point of a blood vessel existing in a position which is closest to the assumed end point position among end points of one or more blood vessels recognized from an eye image when actually measuring cycloduction, as the first information pertaining to the position of the predetermined blood vessel.

13. A cycloduction measurement method, comprising:
acquiring ellipse parameters of a pupil contour by performing ellipse fitting processing on the pupil contour in an eye image of a subject being in a reference state;
recognizing a position of a predetermined blood vessel in a sclera region in an eye image of the subject acquired when actually measuring cycloduction, and acquiring a first information pertaining to the position of the predetermined blood vessel; and
calculating an angle of cycloduction, on the basis of the first information, a second information pertaining to the position of the predetermined blood vessel in the reference state, and the ellipse parameters of the pupil contour.

14. A cycloduction measurement program implemented in an information processing apparatus, for causing the information processing apparatus to perform:
processing of acquiring ellipse parameters of a pupil contour by performing ellipse fitting processing on the pupil contour in an eye image of a subject being in a reference state;
processing of recognizing a position of a predetermined blood vessel in a sclera region in an eye image of the subject acquired when actually measuring cycloduction, and acquiring a first information pertaining to the position of the predetermined blood vessel; and
processing of calculating an angle of cycloduction, on the basis of the first information, a second information pertaining to the position of the predetermined blood vessel in the reference state, and the ellipse parameters of the pupil contour.

* * * * *